United States Patent
Fujita et al.

(10) Patent No.: US 12,171,231 B2
(45) Date of Patent: Dec. 24, 2024

(54) OXADIAZOLE COMPOUNDS OR SALTS THEREOF, AGROHORTICULTURAL FUNGICIDES CONTAINING THE COMPOUNDS, AND METHODS OF USING THE SAME

(71) Applicant: NIHON NOHYAKU CO., LTD., Tokyo (JP)

(72) Inventors: Naoya Fujita, Kawachinagano (JP); Yutaka Kato, Kawachinagano (JP)

(73) Assignee: NIHON NOHYAKU CO., LTD., Tokyo (JP)

(*) Notice: Subject to any disclaimer, the term of this patent is extended or adjusted under 35 U.S.C. 154(b) by 543 days.

(21) Appl. No.: 17/611,977

(22) PCT Filed: Jun. 19, 2020

(86) PCT No.: PCT/JP2020/024162
§ 371 (c)(1),
(2) Date: Nov. 17, 2021

(87) PCT Pub. No.: WO2020/256113
PCT Pub. Date: Dec. 24, 2020

(65) Prior Publication Data
US 2022/0248675 A1    Aug. 11, 2022

(30) Foreign Application Priority Data
Jun. 21, 2019 (JP) .................................. 2019-115157

(51) Int. Cl.
    *A01N 43/82*      (2006.01)
    *A01P 3/00*      (2006.01)
    *C07D 413/04*      (2006.01)

(52) U.S. Cl.
    CPC ............... *A01N 43/82* (2013.01); *A01P 3/00* (2021.08); *C07D 413/04* (2013.01)

(58) Field of Classification Search
    CPC .......... A01N 43/82; A01P 3/00; C07D 413/04
    USPC ....................................................... 514/364
See application file for complete search history.

(56) References Cited

U.S. PATENT DOCUMENTS

2007/0066617 A1    3/2007    Mita et al.
2021/0037823 A1    2/2021    Fujita et al.

FOREIGN PATENT DOCUMENTS

| JP | 63162680 A | 7/1988 |
|---|---|---|
| WO | 2005085216 A1 | 1/2008 |
| WO | 2015185485 A1 | 12/2015 |
| WO | 2017055473 A1 | 4/2017 |
| WO | 2017085098 A1 | 5/2017 |
| WO | 2018117034 A1 | 6/2018 |
| WO | 2018162643 A1 | 9/2018 |
| WO | 2020032071 A1 | 2/2020 |
| WO | 2019131867 A1 | 1/2021 |

*Primary Examiner* — Kristin A Vajda
(74) *Attorney, Agent, or Firm* — RAPHAEL BELLUM PLLC

(57) ABSTRACT

In production of crops of agriculture and horticulture or the like, damage caused by diseases is still large, and, due to factors such as occurrence of resistant diseases to existing drugs, development of new agrohorticultural fungicides is desired. The present invention provides an agrohorticultural fungicide and a method of use thereof, an active ingredient thereof being a compound represented by the general formula (I) or salts thereof:

[Chem 1]

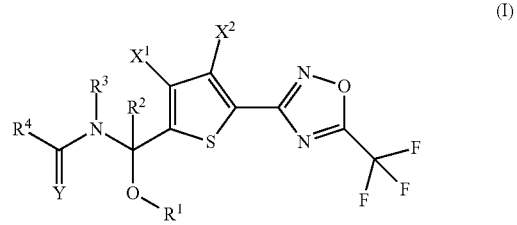

{wherein $R^1$ denotes a hydrogen atom or $(C_1$-$C_6)$alkyl group or the like. $R^2$ denotes a hydrogen atom or the like. $R^3$ denotes a hydrogen atom or $(C_1$-$C_6)$alkyl group or the like. $R^4$ denotes a $(C_1$-$C_6)$alkyl group, $(C_3$-$C_6)$cycloalkyl group or aryl group or the like. $X^1$ and $X^2$ denote a hydrogen atom or halogen atom or the like. Y denotes an oxygen atom.}

6 Claims, No Drawings

OXADIAZOLE COMPOUNDS OR SALTS THEREOF, AGROHORTICULTURAL FUNGICIDES CONTAINING THE COMPOUNDS, AND METHODS OF USING THE SAME

TECHNICAL FIELD

The present invention relates to an agrohorticultural fungicide containing an oxadiazole compound or a salt thereof as an active ingredient, and a method of using the same.

BACKGROUND ART

Patent Document 1, 2 and 3 describe that certain oxadiazole derivatives have fungicidal activity against plant disease causing fungi. These documents fail to disclose or suggest a compound having a hemiaminal structure in the structure of the compound.

CITATION LIST

Patent Document

[Patent Document 1] JP63-162680A
[Patent Document 2] WO2015/185485 pamphlet
[Patent Document 3] WO2017/055473 pamphlet

SUMMARY OF INVENTION

Technical Problem

In production of crops of agriculture and horticulture or the like, damage caused by diseases is still large, and, due to factors such as occurrence of resistant diseases to existing drugs, development of new agrohorticultural fungicides is desired.

Means to Solve the Problem

As a result of intensive research to develop novel fungicides, the present inventors found that the compound represented by the general formula (I) of the present invention or a salt thereof is useful as an agrohorticultural fungicide to complete the present invention.

Namely, the present invention relates to the following:

[1] A compound represented by the general formula (I) or salts thereof:

[Chem 1]

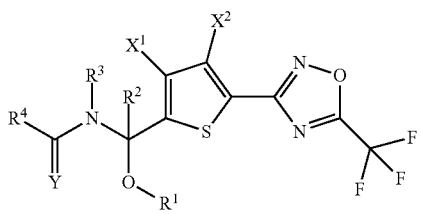

(I)

wherein $R^1$ denotes
(a1) a hydrogen atom;
(a2) a $(C_1-C_6)$alkyl group;
(a3) a $(C_2-C_6)$alkenyl group;
(a4) a $(C_2-C_6)$alkynyl group;
(a5) a $(C_3-C_6)$cycloalkyl group;
(a6) a halo$(C_1-C_6)$alkyl group;
(a7) a halo$(C_2-C_6)$alkenyl group;
(a8) a halo$(C_2-C_6)$alkynyl group; or
(a9) a halo$(C_3-C_8)$cycloalkyl group.

$R^2$ denotes
(b1) a hydrogen atom;
(b2) a $(C_1-C_6)$alkyl group;
(b3) a $(C_2-C_6)$alkenyl group;
(b4) a $(C_2-C_6)$alkynyl group;
(b5) a $(C_3-C_6)$cycloalkyl group;
(b6) a halo$(C_1-C_6)$alkyl group;
(b7) a halo$(C_2-C_6)$alkenyl group;
(b8) a halo$(C_2-C_6)$alkynyl group; or
(b9) a halo$(C_3-C_8)$cycloalkyl group.

$R^3$ denotes
(c1) a hydrogen atom;
(c2) a $(C_1-C_6)$alkyl group;
(c3) a $(C_2-C_6)$alkenyl group;
(c4) a $(C_2-C_6)$alkynyl group;
(c5) a $(C_3-C_6)$cycloalkyl group;
(c6) a $(C_1-C_6)$alkylcarbonyl group; or
(c7) a $(C_1-C_6)$alkoxycarbonyl group.

$R^4$ denotes
(d1) a hydrogen atom;
(d2) a $(C_1-C_6)$alkyl group;
(d3) a $(C_2-C_6)$alkenyl group;
(d4) a $(C_2-C_6)$alkynyl group;
(d5) a $(C_3-C_6)$cycloalkyl group;
(d6) a $(C_1-C_6)$alkoxyl group;
(d7) a halo$(C_1-C_6)$alkyl group;
(d8) a halo$(C_2-C_6)$alkenyl group;
(d9) a halo$(C_2-C_6)$alkynyl group;
(d10) a halo$(C_3-C_8)$cycloalkyl group;
(d11) a halo$(C_1-C_6)$alkoxyl group;
(d12) a $R^a(R^b)N$ group (wherein $R^a$ and $R^b$ each independently denote a hydrogen atom, $(C_1-C_6)$alkyl group, $(C_3-C_6)$cycloalkyl group, $(C_3-C_6)$cycloalkyl$(C_1-C_6)$alkyl group, phenyl group, $(C_1-C_6)$alkylcarbonyl group or phenylcarbonyl group);
(d13) an aryl group;
(d14) an aryl group each independently having on the ring 1 to 8 substituents selected from the group consisting of a halogen atom, cyano group, nitro group, $(C_1-C_6)$alkyl group, $(C_1-C_6)$alkoxy group, $(C_3-C_6)$cycloalkyl group, halo$(C_1-C_6)$alkyl group, halo$(C_1-C_6)$alkoxy group, halo$(C_3-C_6)$cycloalkyl group, $(C_1-C_6)$alkylthio group, $(C_1-C_6)$alkylsulfinyl group, $(C_1-C_6)$alkylsulfonyl group, halo$(C_1-C_6)$alkylthio group, halo$(C_1-C_6)$alkylsulfinyl group and halo$(C_1-C_6)$alkylsulfonyl group);
(d15) a heteroaryl group;
(d16) a heteroaryl group each independently having on the ring 1 to 3 substituents selected from the group consisting of a halogen atom, cyano group, nitro group, $(C_1-C_6)$alkyl group, $(C_1-C_6)$alkoxy group, $(C_3-C_6)$cycloalkyl group, halo$(C_1-C_6)$alkyl group, halo$(C_1-C_6)$alkoxy group, halo$(C_3-C_6)$cycloalkyl group, $(C_1-C_6)$alkylthio group, $(C_1-C_6)$alkylsulfinyl group, $(C_1-C_6)$alkylsulfonyl group, halo$(C_1-C_6)$alkylthio group, halo$(C_1-C_6)$alkylsulfinyl group and halo$(C_1-C_6)$alkylsulfonyl group);
(d17) an aryl$(C_1-C_6)$alkyl group;
(d18) an aryl$(C_1-C_6)$alkyl group each independently having on the ring 1 to 8 substituents selected from the group consisting of a halogen atom, cyano group, nitro group, $(C_1-C_6)$alkyl group, $(C_1-C_6)$alkoxy group, $(C_3-C_6)$cycloalkyl group, halo$(C_1-C_6)$alkyl group, halo$(C_1-$ $C_6$)alkoxy group, halo($C_3$-$C_6$)cycloalkyl group, ($C_1$-$C_6$)alkylthio group, ($C_1$-$C_6$)alkylsulfinyl group, ($C_1$-$C_6$)alkylsulfonyl group, halo($C_1$-$C_6$)alkylthio group, halo($C_1$-$C_6$)alkylsulfinyl group and halo($C_1$-$C_6$)alkylsulfonyl group;

(d19) a heteroaryl($C_1$-$C_6$)alkyl group;

(d20) a heteroaryl($C_1$-$C_6$)alkyl group each independently having on the ring 1 to 3 substituents selected from the group consisting of a halogen atom, cyano group, nitro group, ($C_1$-$C_6$)alkyl group, ($C_1$-$C_6$)alkoxy group, ($C_3$-$C_6$)cycloalkyl group, halo($C_1$-$C_6$)alkyl group, halo($C_1$-$C_6$)alkoxy group, halo($C_3$-$C_6$)cycloalkyl group, ($C_1$-$C_6$)alkylthio group, ($C_1$-$C_6$)alkylsulfinyl group, ($C_1$-$C_6$)alkylsulfonyl group, halo($C_1$-$C_6$)alkylthio group, halo($C_1$-$C_6$)alkylsulfinyl group and halo($C_1$-$C_6$)alkylsulfonyl group;

(d21) a ($C_1$-$C_6$)alkyl group each independently having on the chain 1 to 3 substituents selected from the group consisting of a cyano group, ($C_1$-$C_6$)alkoxyl group, $R^a(R^b)N$ group (wherein $R^a$ and $R^b$ have the same meaning as mentioned above), ($C_1$-$C_6$)alkylthio group, ($C_1$-$C_6$)alkylsulfinyl group and ($C_1$-$C_6$)alkylsulfonyl group; or (d22) a tetrahydropyranyl group.

$X^1$ and $X^2$ each independently denote (e1) a hydrogen atom;

(e2) a halogen atom;

(e3) a cyano group;

(e4) a nitro group;

(e5) a ($C_1$-$C_6$)alkyl group;

(e6) a ($C_3$-$C_6$)cycloalkyl group;

(e7) a ($C_1$-$C_6$)alkoxyl group;

(e8) a halo($C_1$-$C_6$)alkyl group;

(e9) a halo($C_1$-$C_6$)alkoxyl group;

(e10) a halo($C_3$-$C_6$)cycloalkyl group;

(e11) a ($C_1$-$C_6$)alkylthio group;

(e12) a ($C_1$-$C_6$)alkylsulfinyl group;

(e13) a ($C_1$-$C_6$)alkylsulfonyl group;

(e14) a halo($C_1$-$C_6$)alkylthio group;

(e15) a halo($C_1$-$C_6$)alkylsulfinyl group; or (e16) a halo($C_1$-$C_6$)alkylsulfonyl group.

Y denotes an oxygen atom; or a sulfur atom.

[2] The compound according to [1] above or salts thereof, wherein $R^1$ is (a2) a ($C_1$-$C_6$)alkyl group, $R^2$ is (b1) a hydrogen atom, $R^3$ is (c1) a hydrogen atom;

(c2) a ($C_1$-$C_6$)alkyl group; or (c5) a ($C_3$-$C_6$)cycloalkyl group, $R^4$ is (d2) a ($C_1$-$C_6$)alkyl group;

(d3) a ($C_2$-$C_6$)alkenyl group;

(d4) a ($C_2$-$C_6$)alkynyl group;

(d5) a ($C_3$-$C_6$)cycloalkyl group;

(d6) a ($C_1$-$C_6$)alkoxyl group;

(d7) a halo($C_1$-$C_6$)alkyl group;

(d12) a $R^a(R^b)N$ group (wherein $R^a$ and $R^b$ each independently denote a hydrogen atom, ($C_1$-$C_6$)alkyl group, ($C_3$-$C_6$)cycloalkyl group, ($C_3$-$C_6$)cycloalkyl($C_1$-$C_6$)alkyl group, phenyl group, ($C_1$-$C_6$)alkylcarbonyl group or phenylcarbonyl group);

(d13) an aryl group;

(d14) an aryl group each independently having on the ring 1 to 8 substituents selected from the group consisting of a halogen atom, cyano group, nitro group, ($C_1$-$C_6$)alkyl group, ($C_1$-$C_6$)alkoxy group, ($C_3$-$C_6$)cycloalkyl group, halo($C_1$-$C_6$)alkyl group, halo($C_1$-$C_6$)alkoxy group, halo($C_3$-$C_6$)cycloalkyl group, ($C_1$-$C_6$)alkylthio group, ($C_1$-$C_6$)alkylsulfinyl group, ($C_1$-$C_6$)alkylsulfonyl group, halo($C_1$-$C_6$)alkylthio group, halo($C_1$-$C_6$)alkylsulfinyl group and halo($C_1$-$C_6$)alkylsulfonyl group;

(d15) a heteroaryl group;

(d17) an aryl($C_1$-$C_6$)alkyl group;

(d21) a ($C_1$-$C_6$)alkyl group each independently having on the chain 1 to 3 substituents selected from the group consisting of a cyano group, ($C_1$-$C_6$)alkoxyl group, $R^a(R^b)N$ group (wherein $R^a$ and $R^b$ have the same meaning as mentioned above), ($C_1$-$C_6$)alkylthio group, ($C_1$-$C_6$)alkylsulfinyl group and ($C_1$-$C_6$)alkylsulfonyl group; or (d22) a tetrahydropyranyl group, $X^1$ and $X^2$ are each independently (e1) a hydrogen atom;

(e2) a halogen atom;

(e5) a ($C_1$-$C_6$)alkyl group;

(e7) a ($C_1$-$C_6$)alkoxyl group;

(e11) a ($C_1$-$C_6$)alkylthio group;

(e12) a ($C_1$-$C_6$)alkylsulfinyl group; or (e13) a ($C_1$-$C_6$)alkylsulfonyl group, Y is an oxygen atom; or a sulfur atom,

[3] The compound according to [1] or [2] above or salts thereof, wherein $R^3$ is (c1) a hydrogen atom, $R^4$ is (d2) a ($C_1$-$C_6$)alkyl group;

(d4) a ($C_2$-$C_6$)alkynyl group;

(d5) a ($C_3$-$C_6$)cycloalkyl group;

(d7) a halo($C_1$-$C_6$)alkyl group;

(d13) an aryl group; or (d21) a ($C_1$-$C_6$)alkyl group each independently having on the chain 1 to 3 substituents selected from the group consisting of a cyano group, ($C_1$-$C_6$)alkoxyl group, $R^a(R^b)N$ group (wherein $R^a$ and $R^b$ have the same meaning as mentioned above), ($C_1$-$C_6$)alkylthio group, ($C_1$-$C_6$)alkylsulfinyl group and ($C_1$-$C_6$)alkylsulfonyl group, $X^1$ and $X^2$ are each independently (e1) a hydrogen atom, Y is an oxygen atom,

[4] A fungicide characterized in containing as an active ingredient the compound according to any one of [1] to [3] above or salts thereof,

[5] A method of controlling plant disease characterized in treating an effective amount of the fungicide according to [4] above to a plant or soil,

[6] Use of the compound according to any one of [1] to [3] above or salts thereof as a fungicide.

Effect of Invention

The present inventive compound or salts thereof have a remarkable effect as an agrohorticultural fungicide.

Forms for Carrying out Invention

In the definition in the general formula (I) of the present inventive compound, "halo" denotes "halogen atom", representing a chlorine atom, bromine atom, iodine atom or fluorine atom;

"($C_1$-$C_6$)alkyl group" denotes a straight or branched chain alkyl group of carbon atom number 1-6 such as, for example, a methyl group, ethyl group, normal propyl group, iso-propyl group, normal butyl group, iso-butyl group, secondary butyl group, tertiary butyl group, normal pentyl group, iso-pentyl group, tertiary pentyl group, neopentyl group, 2,3-dimethylpropyl group, 1-ethylpropyl group, 1-methylbutyl group, 2-methylbutyl group, normal hexyl group, iso-hexyl group, 2-hexyl group, 3-hexyl group, 2-methylpentyl group, 3-methylpentyl group, 1,1,2-trimethylpropyl group, 3,3-dimethylbutyl group or the like;

"($C_2$-$C_6$)alkenyl group" denotes a straight or branched chain alkenyl group of carbon atom number 2-6 such as, for example, a vinyl group, allyl group, iso-propenyl group, 1-butenyl group, 2-butenyl group, 2-methyl-2-propenyl group, 1-methyl-2-propenyl group, 2-methyl-1-propenyl group, pentenyl group, 1-hexenyl group, 3,3-dimethyl-1-butenyl group, heptenyl group, octenyl group or the like;

"($C_2$-$C_6$)alkynyl group" denotes a straight or branched chain alkynyl group of carbon atom number 2-6 such as, for example, ethynyl group, 1-propynyl group, 2-propynyl group, 1-butynyl group, 2-butynyl group, 3-butynyl group, 3-methyl-1-propynyl group, 2-methyl-3-propynyl group, pentynyl group, 1-hexynyl group, 3-methyl-1-buynyl group, 3,3-dimethyl-1-butynyl group or the like.

"($C_3$-$C_6$)cycloalkyl group" denotes a cyclic alkyl group of carbon atom number 3-6 such as, for example, a cyclopropyl group, cyclobutyl group, cyclopentyl group, cyclohexyl group or the like; as "($C_1$-$C_6$)alkoxy group" included is a straight or branched chain alkoxy group of carbon atom number 1-6 such as, for example, methoxy group, ethoxy group, normal propoxy group, iso-propoxy group, normal butoxy group, secondary butoxy group, tertiary butoxy group, normal pentyloxy group, iso-pentyloxy group, tertiary pentyloxy group, neopentyloxy group, 2,3-dimethylpropyloxy group, 1-ethylpropyloxy group, 1-methylbutyloxy group, normal hexyloxy group, iso-hexyloxy group, 1,1,2-trimethylpropyloxy group or the like;

"($C_1$-$C_6$)alkylthio group" denotes a straight or branched chain alkylthio group of carbon atom number 1-6 such as, for example, a methylthio group, ethylthio group, normal propylthio group, iso-propylthio group, normal butylthio group, secondary butylthio group, tertiary butylthio group, normal pentylthio group, iso-pentylthio group, tertiary pentylthio group, neopentylthio group, 2,3-dimethylpropylthio group, 1-ethylpropylthio group, 1-methylbutylthio group, normal hexylthio group, iso-hexylthio group, 1,1,2-trimethylpropylthio group or the like;

"($C_1$-$C_6$)alkylsulfinyl group" denotes a straight or branched chain alkylsulfinyl group of carbon atom number 1-6 such as, for example, a methyl sulfinyl group, ethyl sulfinyl group, normal propyl sulfinyl group, iso-propyl sulfinyl group, normal butyl sulfinyl group, secondary butyl sulfinyl group, tertiary butyl sulfinyl group, normal pentyl sulfinyl group, iso-pentyl sulfinyl group, tertiary pentyl sulfinyl group, neopentyl sulfinyl group, 2,3-dimethylpropyl sulfinyl group, 1-ethylpropyl sulfinyl group, 1-methylbutyl sulfinyl group, normal hexyl sulfinyl group, iso-hexyl sulfinyl group, 1,1,2-trimethylpropyl sulfinyl group or the like;

"($C_1$-$C_6$)alkylsulfonyl group" denotes a straight or branched chain alkylsulfonyl group of carbon atom number 1-6 such as, for example, a methyl sulfonyl group, ethyl sulfonyl group, normal propyl sulfonyl group, iso-propyl sulfonyl group, normal butyl sulfonyl group, secondary butyl sulfonyl group, tertiary butyl sulfonyl group, normal pentyl sulfonyl group, iso-pentyl sulfonyl group, tertiary pentyl sulfonyl group, neopentyl sulfonyl group, 2,3-dimethylpropyl sulfonyl group, 1-ethylpropyl sulfonyl group, 1-methylbutyl sulfonyl group, normal hexyl sulfonyl group, iso-hexyl sulfonyl group, 1,1,2-trimethylpropyl sulfonyl group or the like.

"($C_1$-$C_6$)alkylcarbonyl group" denotes an alkylcarbonyl group of carbon atom number 2-7 such as those having the above described a ($C_1$-$C_6$)alkyl group or the like such as, for example, an acetyl group, propanoyl group, butanoyl group, 2-methylpropanoyl group, pentanoyl group, 2-methylbutanoyl group, 3-methylbutanoyl group, pivaloyl group, hexanoyl group, cyclopropylcarbonyl group or the like.

"($C_1$-$C_6$)alkoxycarbonyl group" denotes an alkoxycarbonyl group of carbon atom number 2-7 such as those having the above described a ($C_1$-$C_6$)alkoxy group or the like such as, for example, a methoxycarbonyl group, ethoxycarbonyl group, normal propoxycarbonyl group, isopropoxycarbonyl group, normal butoxycarbonyl group, isobutoxycarbonyl group, secondary butoxycarbonyl group, tertiary butoxycarbonyl group, pentyloxycarbonyl group or the like.

The above-mentioned groups such as "($C_1$-$C_6$)alkyl group", "($C_2$-$C_6$)alkenyl group", "($C_2$-$C_6$)alkynyl group", "($C_3$-$C_6$)cycloalkyl group", "($C_1$-$C_6$)alkoxy group" or "($C_1$-$C_6$)alkylthio group", "($C_1$-$C_6$)alkylsulfinyl group" or "($C_1$-$C_6$)alkylsulfonyl group" or the like, can be substituted with one or two or more halogen atoms at substitutable positions and if these groups are substituted with two or more halogen atoms, the halogen atoms may be the same or different. Such halogen-atom substituted groups are each denoted as "halo ($C_1$-$C_6$)alkyl group", "halo($C_2$-$C_6$)alkenyl group", "halo ($C_2$-$C_6$)alkynyl group", "halo($C_3$-$C_6$)cycloalkyl group", "halo ($C_1$-$C_6$)alkoxy group", "halo($C_1$-$C_6$)alkylthio group", "halo($C_1$-$C_6$)alkylsulfinyl group" or a "halo($C_1$-$C_6$)alkylsulfonyl group".

Expressions such as "($C_1$-$C_6$)", "($C_2$-$C_6$)", or "($C_3$-$C_6$)" or the like define a range of the number of carbon atoms in each substituent. In addition, also for a group to which the above mentioned substituent bonds, the above mentioned definition applies; for example, in the case of "($C_1$-$C_6$)alkoxy($C_1$-$C_6$)alkyl group", what is denoted is that a linear or branched alkoxy group of carbon number 1-6 bonds to a linear or branched alkyl group of carbon number 1-6.

"Aryl group" and "aryl" denote an aromatic hydrocarbon group of carbon number 6-10 such as, for example, a phenyl group, naphtyl group or the like.

"Heteroaryl group" and "heteroaryl" denote a monocyclic aromatic heterocyclic group such as, for example, a furyl group, thienyl group, pyridyl group, pyrimidinyl group, pyridazinyl group, pyrazinyl group, pyrrolyl group, imidazolyl group, pyrazolyl group, thiazolyl group, isothiazolyl group, oxazolyl group, isoxazolyl group, oxadiazolyl group, thiadiazolyl group, triazolyl group, tetrazolyl group, triazinyl group or the like.

As the salts of the present inventive compound represented by the general formula (I), for example, inorganic salts such as hydrochloride, sulfate, nitrate, phosphate or the like, organic salts such as acetate, fumarate, malate, oxalate, methanesulfonate, benzenesulfonate, paratoluenesulfonate or the like, and salts with inorganic or organic bases such as sodium ion, potassium ion, calcium ion, trimethyl ammonium or the like.

In some cases, the present inventive compound represented by the general formula (I) and its salt have one or more asymmetry centers in the structural formula and two or more enantiomers and diastereomers exist; the present invention includes all of each enantiomers and mixtures in which they are comprised at any ratios. In addition, the present inventive compound represented by the general formula (I) and a salt thereof in some cases have two stereo isomers resulted from the carbon-carbon in the structural formula, the present invention including all of each stereo isomers and mixtures in which they are comprised at any ratios.

For the present inventive compound represented by the general formula (I), preferable embodiments are recited as follows.

$R^1$ is preferably
(a2) a $(C_1$-$C_6)$alkyl group.
$R^2$ is preferably
(b1) a hydrogen atom.
$R^3$ is preferably
(c1) a hydrogen atom;
(c2) a $(C_1$-$C_6)$alkyl group; or
(c5) a $(C_3$-$C_6)$cycloalkyl group, and more preferably
(c1) a hydrogen atom.
$R^4$ is preferably
(d2) a $(C_1$-$C_6)$alkyl group;
(d3) a $(C_2$-$C_6)$alkenyl group;
(d4) a $(C_2$-$C_6)$alkynyl group;
(d5) a $(C_3$-$C_6)$cycloalkyl group;
(d6) a $(C_1$-$C_6)$alkoxyl group;
(d7) a halo$(C_1$-$C_6)$alkyl group;
(d12) a $R^a(R^b)N$ group (wherein $R^a$ and $R^b$ each independently denote a hydrogen atom, $(C_1$-$C_6)$alkyl group, $(C_3$-$C_6)$cycloalkyl group, $(C_3$-$C_6)$cycloalkyl$(C_1$-$C_6)$alkyl group, phenyl group, $(C_1$-$C_6)$alkylcarbonyl group or phenylcarbonyl group);
(d13) an aryl group;
(d14) an aryl group each independently having on the ring 1 to 8 substituents selected from the group consisting of a halogen atom, cyano group, nitro group, $(C_1$-$C_6)$alkyl group, $(C_1$-$C_6)$alkoxy group, $(C_3$-$C_6)$cycloalkyl group, halo$(C_1$-$C_6)$alkyl group, halo$(C_1$-$C_6)$alkoxy group, halo$(C_3$-$C_6)$cycloalkyl group, $(C_1$-$C_6)$alkylthio group, $(C_1$-$C_6)$alkylsulfinyl group, $(C_1$-$C_6)$alkylsulfonyl group, halo$(C_1$-$C_6)$alkylthio group, halo$(C_1$-$C_6)$alkylsulfinyl group and halo$(C_1$-$C_6)$alkylsulfonyl group);
(d15) a heteroaryl group;
(d17) an aryl$(C_1$-$C_6)$alkyl group;
(d21) a $(C_1$-$C_6)$alkyl group each independently having on the chain 1 to 3 substituents selected from the group consisting of a cyano group, $(C_1$-$C_6)$alkoxyl group, $R^a(R^b)N$ group (wherein $R^a$ and $R^b$ have the same meaning as mentioned above), $(C_1$-$C_6)$alkylthio group, $(C_1$-$C_6)$alkylsulfinyl group and $(C_1$-$C_6)$alkylsulfonyl group; or
(d22) a tetrahydropyranyl group, further preferably,
(d2) a $(C_1$-$C_6)$alkyl group;
(d4) a $(C_2$-$C_6)$alkynyl group;
(d5) a $(C_3$-$C_6)$cycloalkyl group;
(d7) a halo$(C_1$-$C_6)$alkyl group;
(d13) an aryl group; or
(d21) a $(C_1$-$C_6)$alkyl group each independently having on the chain 1 to 3 substituents selected from the group consisting of a cyano group, $(C_1$-$C_6)$alkoxyl group, $R^a(R^b)N$ group (wherein $R^a$ and $R^b$ have the same meaning as mentioned above), $(C_1$-$C_6)$alkylthio group, $(C_1$-$C_6)$alkylsulfinyl group and $(C_1$-$C_6)$alkylsulfonyl group.
$X^1$ and $X^2$ are preferably
(e1) a hydrogen atom;
(e2) a halogen atom;
(e5) a $(C_1$-$C_6)$alkyl group;
(e7) a $(C_1$-$C_6)$alkoxyl group;
(e11) a $(C_1$-$C_6)$alkylthio group;
(e12) a $(C_1$-$C_6)$alkylsulfinyl group; or
(e13) a $(C_1$-$C_6)$alkylsulfonyl group, further preferably,
(e1) a hydrogen atom.
Y is preferably
an oxygen atom.

Various compounds of the present invention can be produced by the following production methods, for example, but a production method of the present compounds is not limited thereto.

Production Method 1

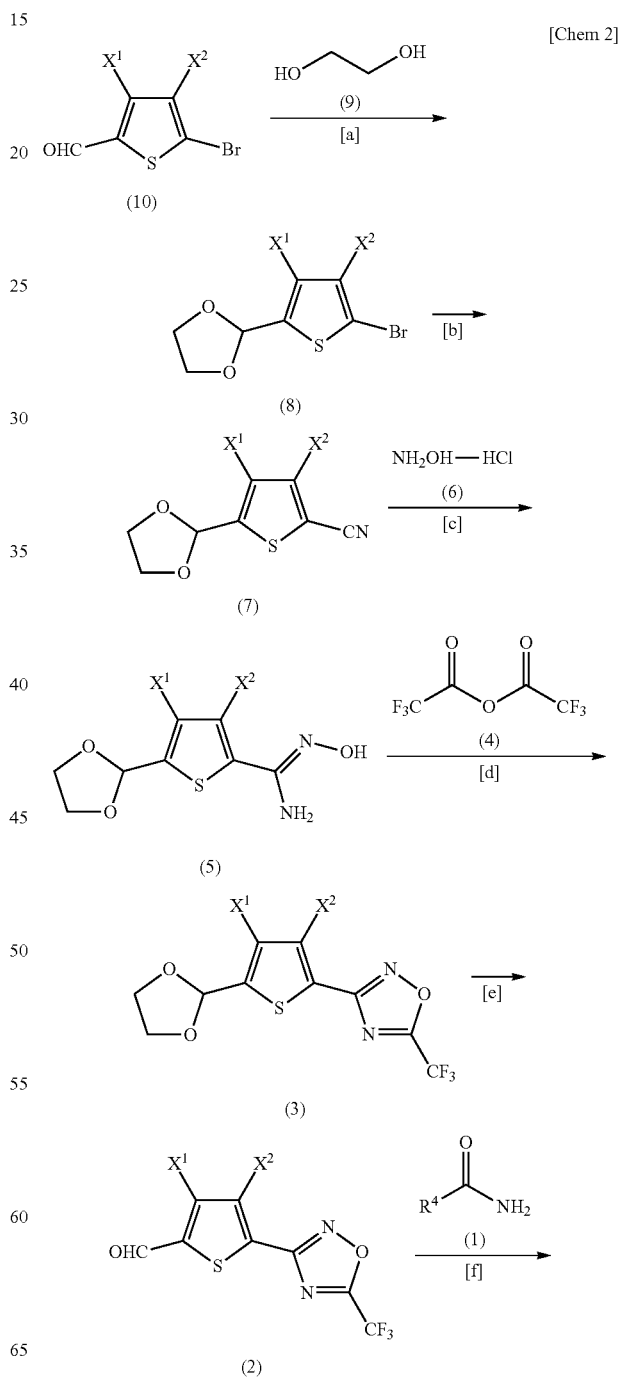

[Chem 2]

-continued

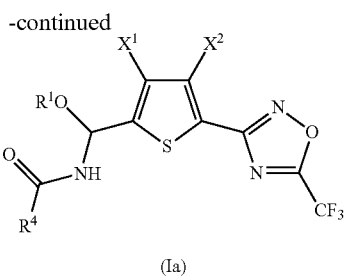

(Ia)

(wherein $R^1$, $R^4$, $X^1$ and $X^2$ denote the same meaning as mentioned above)

The compounds of the present invention represented by the general formula (Ia) can be produced by the following steps [a] to [f].

Step [a] A step for producing a compound represented by the general formula (8) by reacting a compound represented by the general formula (10) with ethylene glycol represented by the formula (9).

Step [b] A step of producing a compound represented by the general formula (7) by cyanizing the compound represented by the general formula (8).

Step [c] A step for producing a compound represented by the general formula (5) by reacting a compound represented by the general formula (7) with a hydroxylamine hydrochloride represented by the formula (6).

Step [d] A step for producing a compound represented by the general formula (3) by reacting a compound represented by the general formula (5) with trifluoroacetic anhydride represented by the formula (4).

Step [e] A step for producing a compound represented by the general formula (2) by deprotecting the compound represented by the general formula (3).

Step [f] A step for producing a compound represented by the general formula (Ia) by reacting the compound represented by the general formula (2) with the compound represented by the general formula (1).

Production Method in Step [a]

The compound represented by the general formula (8) can be produced by reacting the compound represented by the general formula (10) with ethylene glycol represented by the formula (9).

As an acid catalyst that can be used in this reaction, for example, methylsulfonic acid, p-toluene sulfonic acid, trifluoromethanesulfonic acid or the like can be recited; the amount to be used may be selected usually from a range between 0.01 times mole to five times mole with respect to the compound represented by the general formula (10).

As the inert solvent used in this reaction, any solvent which does not significantly inhibit the progress of this reaction may be used; those which can be recited are, for example, aliphatic hydrocarbons such as pentane, hexane and cyclohexane or the like; aromatic hydrocarbons such as benzene, toluene and xylene or the like; halogenated hydrocarbons such as methylene chloride, chloroform and carbon tetrachloride or the like; halogenated aromatic hydrocarbons such as chlorobenzene and dichlorobenzene or the like. These inert solvents may be used alone or in a mixture of two or more. The amount to be used thereof may usually be selected from the range of 0.1 to 100 L with respect to 1 mole of the compound represented by the general formula (10).

Since the reaction is an equimolar reaction, equimolar amounts of each reactant may be used, and any reactant may be used in excess. The reaction temperature can be usually from room temperature to the boiling point range of the inert solvent used, and the reaction time, which varies depending on the reaction scale and reaction temperature, may be usually from several minutes to 48 hours. After completion of the reaction, the target product may be isolated from the reaction system containing the target product by an ordinary method, and the target product can be produced by purification by recrystallization, column chromatography or the like, where necessary.

Production Method in Step [b]

The compound represented by the general formula (7) can be produced by reacting the compound represented by the general formula (8) with copper (I) cyanide in the presence of an inert solvent.

As the inert solvent used in this reaction, any solvent which does not significantly inhibit the progress of this reaction may be used; those which can be recited are, for example, aliphatic hydrocarbons such as pentane, hexane and cyclohexane or the like; aromatic hydrocarbons such as benzene, toluene and xylene or the like; halogenated hydrocarbons such as methylene chloride, chloroform and carbon tetrachloride or the like; halogenated aromatic hydrocarbons such as chlorobenzene and dichlorobenzene or the like; esters such as ethyl acetate and propyl acetate or the like; nitriles such as acetonitrile and propionitrile or the like; amides such as dimethylformamide and dimethylacetamide or the like; ketones such as acetone and methylethylketone or the like; aprotonic polar solvents such as dimethyl sulfoxide and 1,3-dimethyl-2-imidazolidinone or the like. These inert solvents may be used alone or in a mixture of two or more. The amount to be used thereof may usually be selected from the range of 0.1 to 100 L with respect to 1 mole of the compound represented by the general formula (8).

Since the reaction is an equimolar reaction, equimolar amounts of each reactant may be used, and any reactant may be used in excess. The reaction temperature can be usually from room temperature to the boiling point range of the inert solvent used, and the reaction time, which varies depending on the reaction scale and reaction temperature, may be usually from several minutes to 48 hours. After completion of the reaction, the target product may be isolated from the reaction system containing the target product by an ordinary method, and the target product can be produced by purification by recrystallization, column chromatography or the like, where necessary.

Production Method in Step [c]

The compound represented by the general formula (5) by reacting the compound represented by the general formula (7) with the hydroxylamine hydrochloride represented by the formula (6) in the presence of a base and an inert solvent.

As the base which can be used in this reaction and recited are, for example, hydroxides such as lithium hydroxide, sodium hydroxide, potassium hydroxide and calcium hydroxide or the like; alkoxides such as sodium methoxide, sodium ethoxide, sodium tertiary butoxide and potassium tertiary butoxide or the like; carbonates such as lithium carbonate, lithium hydrogen carbonate, sodium carbonate, sodium hydrogen carbonate, potassium carbonate, potassium hydrogen carbonate, calcium carbonate and magnesium carbonate or the like; acetates such as lithium acetate, sodium acetate and potassium acetate or the like; organic bases such as pyridine, picoline, lutidine, triethylamine, tributylamine and diisopropylethylamine or the like. The amount to be used thereof is relative to the compound represented by the general formula (7) may usually be selected from the range of 1 times mol to 10 times mol.

As the inert solvent used in this reaction, any solvent which does not significantly inhibit the progress of this reaction may be used; those which can be recited are, for example, amides such as dimethylformamide and dimethylacetamide or the like; aprotic polar solvents such as dimethyl sulfoxide and 1,3-dimethyl-2-imidazolidinone or the like; inert solvents such as alcohols such as methanol, ethanol and 2-propanol or the like. These inert solvents may be used alone or in a mixture of two or more. The amount to be used thereof may usually be selected from the range of 0.1 to 100 L with respect to 1 mole of the compound represented by the general formula (7).

Since the reaction is an equimolar reaction, equimolar amounts of each reactant may be used, and any reactant may be used in excess. The reaction temperature can be usually from room temperature to the boiling point range of the inert solvent used, and the reaction time, which varies depending on the reaction scale and reaction temperature, may be usually from several minutes to 48 hours. After completion of the reaction, the target product may be isolated from the reaction system containing the target product by an ordinary method, and the target product can be produced by purification by recrystallization, column chromatography or the like, where necessary.

Production Method in Step [d]

The compound represented by the general formula (3) by reacting a compound represented by the general formula (5) with trifluoroacetic anhydride represented by the formula (4) in the presence of a base and an inert solvent.

As the base which can be used in this reaction and recited are, for example, hydroxides such as lithium hydroxide, sodium hydroxide, potassium hydroxide and calcium hydroxide or the like; alkoxides such as sodium methoxide, sodium ethoxide, sodium tertiary butoxide and potassium tertiary butoxide or the like; carbonates such as lithium carbonate, lithium hydrogen carbonate, sodium carbonate, sodium hydrogen carbonate, potassium carbonate, potassium hydrogen carbonate, calcium carbonate and magnesium carbonate or the like; acetates such as lithium acetate, sodium acetate and potassium acetate or the like; organic bases such as pyridine, picoline, lutidine, triethylamine, tributylamine and diisopropylethylamine or the like. The amount to be used thereof is relative to the compound represented by the general formula (5) may usually be selected from the range of 1 times mol to 10 times mol.

As the inert solvent used in this reaction, any solvent which does not significantly inhibit the progress of this reaction may be used; those which can be recited are, for example, aliphatic hydrocarbons such as pentane, hexane and cyclohexane or the like; aromatic hydrocarbons such as benzene, toluene and xylene or the like; halogenated hydrocarbons such as methylene chloride, chloroform and carbon tetrachloride or the like; halogenated aromatic hydrocarbons such as chlorobenzene and dichlorobenzene or the like; esters such as ethyl acetate and propyl acetate or the like; nitriles such as acetonitrile and propionitrile or the like; amides such as dimethylformamide and dimethylacetamide or the like; ketones such as acetone and methylethylketone or the like; aprotonic polar solvents such as dimethyl sulfoxide and 1,3-dimethyl-2-imidazolidinone or the like. These inert solvents may be used alone or in a mixture of two or more. The amount to be used thereof may usually be selected from the range of 0.1 to 100 L with respect to 1 mole of the compound represented by the general formula (5).

Since the reaction is an equimolar reaction, equimolar amounts of each reactant may be used, and any reactant may be used in excess. The reaction temperature can be usually from room temperature to the boiling point range of the inert solvent used, and the reaction time, which varies depending on the reaction scale and reaction temperature, may be usually from several minutes to 48 hours. After completion of the reaction, the target product may be isolated from the reaction system containing the target product by an ordinary method, and the target product can be produced by purification by recrystallization, column chromatography or the like, where necessary.

Production Method in Step [e]

The compound represented by the general formula (2) can be produced by deprotecting the acetal-protected aldehyde group of the compound represented by the general formula (3) by a deprotection reaction generally used in organic chemistry.

Production Method in Step [f]

The compound represented by the general formula (Ia) can be produced by reacting the compound represented by the general formula (2) with the compound represented by the general formula (1) and a titanium compound in the presence of an inert solvent.

As the titanium compound which can be used in this reaction and recited are, for example, titanium(IV) methoxide, titanium(IV) ethoxide, titanium(IV) n-propoxide, titanium(IV) i-propoxide, titanium(IV) n-butoxide and titanium (IV) t-butoxide or the like. The amount to be used can be selected appropriately from the range of 1 to 5 times molar to the compound represented by the general formula (2).

As the inert solvent used in this reaction, any solvent which does not significantly inhibit the progress of this reaction may be used; those which can be recited are, for example, aliphatic hydrocarbons such as pentane, hexane and cyclohexane or the like; aromatic hydrocarbons such as benzene, toluene and xylene or the like; halogenated hydrocarbons such as methylene chloride, chloroform and carbon tetrachloride or the like; halogenated aromatic hydrocarbons such as chlorobenzene and dichlorobenzene or the like; esters such as ethyl acetate and propyl acetate or the like; nitriles such as acetonitrile and propionitrile or the like; amides such as dimethylformamide and dimethylacetamide or the like; ketones such as acetone and methylethylketone or the like; aprotonic polar solvents such as dimethyl sulfoxide and 1,3-dimethyl-2-imidazolidinone or the like. These inert solvents may be used alone or in a mixture of two or more. The amount to be used thereof may usually be selected from the range of 0.1 to 100 L with respect to 1 mole of the compound represented by the general formula (2).

Since the reaction is an equimolar reaction, equimolar amounts of each reactant may be used, and any reactant may be used in excess. The reaction temperature can be usually from room temperature to the boiling point range of the inert solvent used, and the reaction time, which varies depending on the reaction scale and reaction temperature, may be usually from several minutes to 48 hours. After completion of the reaction, the target product may be isolated from the reaction system containing the target product by an ordinary method, and the target product can be produced by purification by recrystallization, column chromatography or the like, where necessary.

Representative examples of the compounds represented by the general formula (I) of the present invention are exemplified below in Tables 1 to 2, but the present invention is not limited thereto.

In the Tables, "Me" denotes a methyl group, "Et" denotes an ethyl group, "n-Pr" denotes a n-propyl group, "i-Pr" denotes an iso-propyl group, "c-Pr" denotes a cyclopropyl group, "n-Bu" denotes a n-butyl group, "i-Bu" denotes an iso-butyl group, "s-Bu" denotes a secondary butyl group, "t-Bu" denotes a tertiary butyl group, "n-Pen" denotes a n-pentyl group, "c-Pen" denotes a cyclopentyl group and "Ph" denotes a phenyl group. Physical properties denote a melting point (° C.) or refractive index $n_D$ (measurement temperature).

[Chem 3]

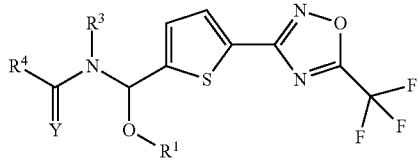

(Ib)

TABLE 1

| Compound No. | $R^1$ | $R^3$ | $R^4$ | Y | Physical properties |
|---|---|---|---|---|---|
| 1-1 | Me | H | Me | O | 159-160 |
| 1-2 | Et | H | Me | O | |
| 1-3 | i-Pr | H | Me | O | |
| 1-4 | n-Pr | H | Me | O | |
| 1-5 | n-Bu | H | Me | O | |
| 1-6 | i-Bu | H | Me | O | |
| 1-7 | Me | H | Et | O | |
| 1-8 | Et | H | Et | O | |
| 1-9 | i-Pr | H | Et | O | |
| 1-10 | n-Pr | H | Et | O | |
| 1-11 | n-Bu | H | Et | O | |
| 1-12 | i-Bu | H | Et | O | |
| 1-13 | Me | H | n-Pr | O | 141-148 |
| 1-14 | Et | H | n-Pr | O | |
| 1-15 | i-Pr | H | n-Pr | O | |
| 1-16 | n-Pr | H | n-Pr | O | |
| 1-17 | n-Bu | H | n-Pr | O | |
| 1-18 | i-Bu | H | n-Pr | O | |
| 1-19 | Me | Me | n-Pr | O | |
| 1-20 | Me | Et | n-Pr | O | |
| 1-21 | Me | c-Pr | n-Pr | O | |
| 1-22 | Me | H | i-Pr | O | 169-170 |
| 1-23 | Et | H | i-Pr | O | |
| 1-24 | i-Pr | H | i-Pr | O | |
| 1-25 | Me | H | c-Pr | O | 187-188 |
| 1-26 | Et | H | c-Pr | O | |
| 1-27 | i-Pr | H | c-Pr | O | |
| 1-28 | Me | H | n-Bu | O | |
| 1-29 | Et | H | n-Bu | O | |
| 1-30 | i-Pr | H | n-Bu | O | |
| 1-31 | Me | H | i-Bu | O | |
| 1-32 | Et | H | i-Bu | O | |
| 1-33 | i-Pr | H | i-Bu | O | |
| 1-34 | Me | H | s-Bu | O | |
| 1-35 | Et | H | s-Bu | O | |
| 1-36 | i-Pr | H | s-Bu | O | |
| 1-37 | Me | H | t-Bu | O | |
| 1-38 | Et | H | t-Bu | O | |
| 1-39 | i-Pr | H | t-Bu | O | |
| 1-40 | Me | H | n-Pen | O | |
| 1-41 | Me | H | vinyl | O | |
| 1-42 | Me | H | 2-propenyl | O | |
| 1-43 | Me | H | Ph | O | 176-177 |
| 1-44 | Et | H | OEt | O | |
| 1-45 | Et | H | Oi-Pr | O | |
| 1-46 | Me | H | CH$_3$Ph | O | |
| 1-47 | Me | H | CF$_3$ | O | 143-144 |
| 1-48 | Me | H | NMe$_2$ | O | |
| 1-49 | Me | H | 1-naphtyl | O | |
| 1-50 | Me | H | 2-naphtyl | O | |
| 1-51 | Me | H | 2-pyridyl | O | |
| 1-52 | Me | H | 3-pyridyl | O | |
| 1-53 | Me | H | 4-pyridyl | O | |
| 1-54 | Me | H | 2-F—Ph | O | |
| 1-55 | Me | H | 3-F—Ph | O | |
| 1-56 | Me | H | 4-F—Ph | O | |
| 1-57 | Me | H | 2-Cl—Ph | O | |
| 1-58 | Me | H | 3-Cl—Ph | O | |
| 1-59 | Me | H | 4-Cl—Ph | O | |
| 1-60 | Me | H | 2-Br—Ph | O | |
| 1-61 | Me | H | 3-Br—Ph | O | |
| 1-62 | Me | H | 4-Br—Ph | O | |
| 1-63 | Me | H | 2-I—Ph | O | |
| 1-64 | Me | H | 3-I—Ph | O | |
| 1-65 | Me | H | 4-I—Ph | O | |
| 1-66 | Me | H | 2-Me—Ph | O | |
| 1-67 | Me | H | 3-Me—Ph | O | |
| 1-68 | Me | H | 4-Me—Ph | O | |
| 1-69 | Me | H | 2-OMe—Ph | O | |
| 1-70 | Me | H | 3-OMe—Ph | O | |
| 1-71 | Me | H | 4-OMe—Ph | O | |
| 1-72 | Me | H | 2-OEt—Ph | O | |
| 1-73 | Me | H | 3-OEt—Ph | O | |
| 1-74 | Me | H | 4-OEt—Ph | O | |
| 1-75 | Me | H | 2-NO$_2$—Ph | O | |
| 1-76 | Me | H | 3-NO$_2$—Ph | O | |
| 1-77 | Me | H | 4-NO$_2$—Ph | O | |
| 1-78 | Me | H | 2,6-di-F—Ph | O | |
| 1-79 | Me | H | 3,5-di-OMe—Ph | O | |
| 1-80 | Me | H | 2,6-di-Cl—Ph | O | |
| 1-81 | Me | H | 2,4-di-Cl—Ph | O | |
| 1-82 | Me | H | CH$_2$Cl | O | |
| 1-83 | Me | H | CH$_2$CN | O | |
| 1-84 | Me | H | n-Pr | S | |
| 1-85 | Et | H | n-Pr | S | |
| 1-86 | i-Pr | H | n-Pr | S | |
| 1-87 | Me | Me | n-Pr | S | |
| 1-88 | Me | Et | n-Pr | S | |
| 1-89 | Me | c-Pr | n-Pr | S | |
| 1-90 | Me | H | OMe | O | |
| 1-91 | Me | H | CH$_2$OMe | O | 108-110 |
| 1-92 | Me | H | CH$_2$OEt | O | |
| 1-93 | Me | H | CH$_2$NHMe | O | |
| 1-94 | Me | H | CH$_2$NHEt | O | |
| 1-95 | Me | H | CH$_2$SMe | O | |
| 1-96 | Me | H | CH$_2$S(O)Me | O | |
| 1-97 | Me | H | CH$_2$S(O)$_2$OMe | O | |
| 1-98 | Me | H | CH$_2$SEt | O | |
| 1-99 | Me | H | CH$_2$S(O)Et | O | |
| 1-100 | Me | H | CH$_2$S(O)$_2$Et | O | |
| 1-101 | Me | H | CHCl$_2$ | O | 140-142 |
| 1-102 | Me | H | CCl$_3$ | O | |
| 1-103 | Me | H | CF$_2$CF$_3$ | O | |
| 1-104 | Me | H | CH=CHMe | O | |
| 1-105 | Me | H | CHF$_2$ | O | |
| 1-106 | Me | H | CF$_2$Br | O | |
| 1-107 | Me | H | C≡CH | O | 129-130 |
| 1-108 | Me | H | c-Pen | O | |
| 1-109 | Me | H | ![tetrahydropyran] | O | 176-177 |
| 1-110 | Me | H | CH$_2$CH$_2$OMe | O | |
| 1-111 | Me | H | CH$_2$CH$_2$OEt | O | |
| 1-112 | Et | H | CH$_2$OMe | O | |
| 1-113 | Me | H | 2-pyridyl | O | |
| 1-114 | Me | H | 3-pyridyl | O | |
| 1-115 | Me | H | 4-pyridyl | O | |

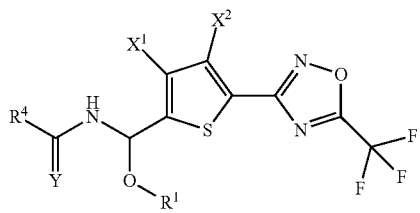

(Ia)

TABLE 2

| Compound No. | R¹ | R⁴ | X¹ | X² | Physical properties |
|---|---|---|---|---|---|
| 2-1 | Me | n-Pr | Me | H | |
| 2-2 | Me | n-Pr | H | Me | |
| 2-3 | Me | n-Pr | Cl | H | |
| 2-4 | Me | n-Pr | H | Cl | |
| 2-5 | Et | OEt | H | F | |
| 2-6 | Me | n-Pr | H | F | |
| 2-7 | Me | Ph | H | F | |
| 2-8 | Me | CF₃ | H | F | |
| 2-9 | Me | Et | H | F | |
| 2-10 | Me | i-Pr | H | F | |
| 2-11 | Me | c-Pr | H | F | |
| 2-12 | Me | t-Bu | H | F | |
| 2-13 | Me | C≡CH | H | F | |
| 2-14 | Me | 2-F—Ph | H | F | |
| 2-15 | Me | 2-Cl—Ph | H | F | |
| 2-16 | Me | 2-OMe—Ph | H | F | |
| 2-17 | Me | 2-pyridyl | F | F | |
| 2-18 | Me | 3-pyridyl | H | F | |
| 2-19 | Me | 4-pyridyl | H | F | |
| 2-20 | Me | n-Pr | OMe | H | |
| 2-21 | Me | Ph | OMe | H | |
| 2-22 | Me | CF₃ | OMe | H | |
| 2-23 | Me | n-Pr | F | H | |
| 2-24 | Me | Ph | F | H | |
| 2-25 | Me | CH₂NMe₂ | H | H | |
| 2-26 | Me | n-Pr | SMe | H | |
| 2-27 | Me | Ph | SMe | H | |
| 2-28 | Me | n-Pr | S(O)₂Me | H | |
| 2-29 | Me | n-Pr | S(O)Me | H | |
| 2-30 | Me | n-Pr | S(O)Me | H | |
| 2-31 | Me | Ph | S(O)₂Me | H | |
| 2-32 | Me | Ph | S(O)Me | H | |
| 2-33 | Me | Ph | S(O)Me | H | |
| 2-34 | Me | CH₂OMe | Me | H | |
| 2-35 | Me | CH₂OMe | H | F | |
| 2-36 | Me | CH₂OMe | F | H | |
| 2-37 | Me | Et | F | H | |
| 2-38 | Me | i-Pr | F | H | |
| 2-39 | Me | c-Pr | F | H | |
| 2-40 | Me | i-Bu | F | H | |
| 2-41 | Me | C≡CH | F | H | |
| 2-42 | Me | 2-F—Ph | F | H | |
| 2-43 | Me | 2-Cl—Ph | F | H | |
| 2-44 | Me | 2-OMe—Ph | F | H | |
| 2-45 | Me | 2-pyridyl | F | H | |
| 2-46 | Me | 3-pyridyl | F | H | |
| 2-47 | Me | 4-pyridyl | F | H | |
| 2-48 | Me | CHCl₂ | F | H | |
| 2-49 | Me | CHCl₂ | H | F | |

Agrohorticultural fungicides containing the compound represented by the general formula (I) of the present invention or a salt thereof as an active ingredient are suitable for controlling diseases which occur on cereals, fruits, vegetables, other crops and ornamental plants.

Target diseases include filamentous fungal diseases, bacterial diseases, viral diseases or the like. The filamentous fungal diseases that can be recited are, for example, diseases caused by fungi-imperfecti (*Botrytis* diseases, *Helminthosporium* diseases, *Fusarium* diseases, *Septoria* diseases, *Cercospora* diseases, *Pseudocercosporella* diseases, *Rhynchosporium* diseases, *Pyricularia* diseases and *Alternaria* diseases or the like); diseases caused by basidiomycetes (for example, *Hemilelia* diseases, *Rhizoctonia* diseases, *Ustilago* diseases, *Typhula* diseases and *Puccinia* diseases or the like); diseases caused by ascomycota (for example, *Venturia* diseases, *Podosphaera* diseases, *Leptosphaeria* diseases, *Blumeria* diseases, *Erysiphe* diseases, *Microdochium* diseases, *Sclerotinia* diseases, *Gaeumannomyces* diseases, *Monilinia* diseases and *Unsinula* diseases or the like); and diseases caused by other fungi (for example, *Ascochyta* diseases, *Phoma* diseases, *Pythium* diseases, *Corticium* diseases and *Pyrenophora* diseases or the like). As the bacterial diseases that can be recited are, for example, *Pseudomonas* diseases, *Xanthomonas* diseases and *Erwinia* diseases or the like. As the viral diseases, for example, disease such as those caused by tobacco mosaic virus or the like is recited.

Specific filamentous fungal disease that can be recited are, for example, rice blast (*Pyricularia oryzae*), rice sheath blight (*Rhizoctonia solani*), rice brown spot (*Cochiobolus miyabeanus*), rice seedling blight (*Rhizopus chinensis, Pythium graminicola, Fusarium graminicola, Fusarium roseum, Mucor* sp., *Phoma* sp., *Tricoderma* sp.), rice bakanae disease (*Gibberella fujikuroi*), powdery mildew in barley and wheat or the like (*Blumeria graminis*), powdery mildew in cucumbers or the like (*Sphaerotheca fuliginea*), powdery mildew in eggplants or the like (*Erysiphe cichoracoarum*) and powdery mildew in other host plants, eyespot in barley, wheat, or the like (*Pseudocercosporella herpotrichoides*), smut in wheat or the like (*Urocystis tritici*), snow mold in barley, wheat or the like (*Microdochium nivalis, Pythium iwayamai, Typhla ishikariensis, Typhla incarnata, Sclerotinia borealis*), fusarium ear blight in barley, wheat or the like (*Fusarium graminearum, Fusarium avenaceum, Fusarium culmorum, Microdochium nivalis*), rust in barley, wheat or the like (*Puccinia recondita, Puccinia striiformis, Puccinia graminis*), take-all in barley, wheat or the like (*Gaeumannomyces graminis*), oat crown rust (*Puccinia coronata*), rust in other plants, gray mold in cucumbers, strawberries or the like (*Botrytis cinerea*), sclerotinia rot in tomatoes, cabbages or the like (*Sclerotinia sclerotiorum*), late blight in potatoes, tomatoes or the like (*Phytophthora infestans*), late blight in other plants, cucumber downy mildew (*Pseudoperonospora cubensis*), grape downy mildew (*Plasmopara viticola*), downy mildew in various plants, apple scab (*Venturia inaequalis*), apple alternaria blotch (*Alternaria mali*), pear black spot (*Alternaria kikuchiana*), citrus melanose (*Diaporthe citri*), citrus scab (*Elsinoe fawcetti*), sugarbeet leaf spot (*Cercospora beticola*), peanut brown leaf spot (*Cercospora arachidicola*), peanut late leaf spot (*Cercospora personata*), leaf blotch in wheat (*Septoria tritici*), wheat glume blotch (*Leptosphaeria nodorum*), barley net blotch (*Pyrenophora teres*), barley stripe (*Pyrenophora graminea*), barley scald (*Rhynchosporium secalis*), wheat loose smut (*Ustilago nuda*), wheat stinking smut (*Tilletia caries*), brown patch in turfgrass (*Rhizoctonia solani*) and dollar spot in turfgrass (*Sclerotinia homoeocarpa*) or the like.

Specific bacterial diseases that can be recited are diseases caused by *Pseudomonas* spp., for example, cucumber bacterial spot (*Pseudomonas syringae* pv. *lachrymans*), tomato bacterial wilt disease (*Pseudomonas solanacearum*) and bacterial grain rot of rice (*Pseudomonas glumae*); diseases caused by *Xanthomonas* spp., for example, cabbage black rot (*Xanthomonas campestris*), rice bacterial leaf blight (*Xanthomonas oryzae*) and citrus canker (*Xanthomonas* citri); and diseases caused by *Erwinia* spp., for example, cabbage soft rot (*Erwinia carotovora*) or the like.

The useful plants on which the present inventive compound represented by the general formula (I) or salts thereof can be applied are not particularly limited, and the following plants can be recited as examples thereof:

cereals (for example, rice, barley, wheat, rye, oat, corn or the like); beans and peas such as soybean, red bean, broad bean, pea, kidney-bean, peanut or the like; fruit trees (for example, apple, citrus trees and fruits, pear, grape, peach, plum, cherry, walnut, chestnut, almond, banana or the like); leafy and fruit vegetables (for example, cabbage, tomato, spinach, broccoli, lettuce, onion, green onions (chives and Welsh onions), green peppers, eggplant, strawberry, pepper, okra, Chinese chives or the like); root crops (for example, carrot, potato, sweet potato, taro, radish, lotus rhizome, turnip, burdock, garlic, Chinese scallions or the like); processing crops (for example, cotton, flax, beet, hop, sugar can, sugar beet, olive, gum, coffee, tobacco, tea or the like); cucurbitaceous plants (for example, pumpkin, cucumber, water melon, oriental melon, melon or the like); pasture plants (for example, orchard grass, sorghum, timothy, clover, alfalfa or the like); lawn grasses (for example, mascarenegrass, bent grass or the like); perfumery crops (for example, lavender, rosemary, thyme, parsley, pepper, ginger or the like); flowers and ornamental plants (for example, chrysanthemum, rose, carnation, orchid, tulip, lily or the like); garden-trees (for example, ginkgo tree, cherry tree, aucuba or the like); and timber woods (for example, white fir, silver fir, pine, hatchet-leaved arbor-vitae, Japan cedar, Japanese eypress, eukalyptus or the like).

The aforementioned "plants" also include those to which resistance to HPPD inhibitors such as isoxaflutole, ALS inhibitors such as imazethapyr or thifensulfuron-methyl, EPSP synthetase inhibitors such as glyphosate, glutamine synthetase inhibitors such as glufosinate, acetyl-CoA carboxylase inhibitors such as sethoxydim and herbicides such as bromoxynil, dicamba, 2,4-D or the like has been conferred by a classical breeding method or genetic engineering technique.

Examples of the "plant" to which resistance has been conferred by a classical breeding method include rape, wheat, sunflower and rice resistant to imidazolinone ALS inhibitory herbicides such as imazethapyr, which are already commercially available under a product name of Clearfield (registered trademark). Likewise there is soy bean to which resistance to sulfonylurea ALS inhibitory herbicides such as thifensulfuron-methyl has been conferred by a classical breeding method, which is already commercially available under a product name of STS soy bean. Likewise examples to which resistance to acetyl-CoA carboxylase inhibitors such as trione oxime or aryloxy phenoxypropionic acid herbicides has been conferred by a classical breeding method include SR corn.

The plant to which resistance to acetyl-CoA carboxylase inhibitors has been conferred is described in Proceedings of the National Academy of Sciences of the United States of America (Proc. Natl. Acad. Sci. USA), vol. 87, pp. 7175-7179 (1990) or the like. A variation of acetyl-CoA carboxylase resistant to an acetyl-CoA carboxylase inhibitor is reported in Weed Science, vol. 53, pp. 728-746 (2005) or the like and a plant resistant to acetyl-CoA carboxylase inhibitors can be generated by introducing a gene of such an acetyl-CoA carboxylase variation into a plant by genetically engineering technology or by introducing a variation conferring resistance into a plant acetyl-CoA carboxylase; furthermore, plants resistant to acetyl-CoA carboxylase inhibitors or ALS inhibitors or the like can be generated by introducing a site-directed amino acid substitution variation into an acetyl-CoA carboxylase gene or the ALS gene of the plant by introduction a nucleic acid into which has been introduced a base substitution variation represented Chimeraplasty Technique (Gura T. 1999. Repairing the Genome's Spelling Mistakes. Science 285: 316-318) into a plant cell. The present inventive compound represented by the general formula (I) or salts thereof can be used for these plants as well.

In addition examples of toxins expressed in such genetically engineered crops include: insecticidal proteins derived from *Bacillus cereus* or *Bacillus popilliae*; endotoxins such as CrylAb, CrylAc, CrylF, CrylFa2, Cry2Ab, Cry3A, Cry3Bbl or Cry9C derived from *Bacillus thuringiensis*; insecticidal proteins such as VIP1, VIP2, VIP3 or VIP3A; insecticidal proteins derived from nematodes; toxins generated by animals such as scorpion toxin, spider toxin, bee toxin or insect-specific neurotoxins; mold fungi toxins; plant lectin; agglutinin; protease inhibitors such as a trypsin inhibitor, a serine protease inhibitor, patatin, cystatin or a papain inhibitor; ribosome-inactivating proteins (RIP) such as lycine, corn-RIP, abrin, luffin, saporin or briodin; steroid-metabolizing enzymes such as 3-hydroxysteroid oxidase, ecdysteroid-UDP-glucosyl transferase or cholesterol oxidase; an ecdysone inhibitor; HMG-CoA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Furthermore, toxins expressed in such genetically engineered crops also include: hybrid toxins, partially deleted toxins and modified toxins of δ-endotoxin proteins such as CrylAb, CrylAc, CrylF, CrylFa2, Cry2Ab, Cry3A, Cry3Bbl, Cry9C, Cry34Ab or Cry35Ab; insecticidal proteins such as VIP1, VIP2, VIP3 or VIP3A. The hybrid toxins are produced from a new combination of the different domains of such proteins, using a genetic engineering technique. As the partially deleted toxins, CrylAb comprising a deletion of a portion of an amino acid sequence is known. In the modified toxins one or more amino acids of natural toxins are substituted.

Examples of such toxins and genetically engineered plants capable of synthesizing such toxins are described in EP-A-0 374 753, WO 93/07278, WO 95/34656, EP-A-0 427 529, EP-A-451 878, WO 03/052073 or the like.

The present inventive agrohorticultural fungicide can also be used in combination, or systematically, with such technologies.

In order to control various diseases, the present inventive agrohorticultural fungicide is applied to the plants on which emergence of the diseases is expected, either as it is or in the form of a dilution or suspension in a proper quantity of water or the like at a dosage effective for the control of the diseases. For instance, with the aim of controlling the appearance of diseases on fruit trees, cereals and vegetables, the composition may be directly used for foliage treatment or the composition may also be used for seed treatments such as immersion of seeds in the agent solution, seed coating, calper treatment or the like or absorption from the root by soil treatment or the like, such as incorporation into total soil layer, row treatment, soil incorporation, cell seedling treatment, prickling-in-hole treatment, plant foot treatment, top dressing, nursery box application of rice, submerged application or the like. In addition, application oft the present inventive agrohorticultural insecticide to the nutrient solution in the water culture, the use by fumigation, and the injection into tree stalks or the like are also usable.

Furthermore, the present inventive agrohorticultural fungicide may be used as it is or with appropriate dilution with water or the like, or in suspension, in an amount effective for disease control to a site where occurrence of the disease is expected.

As the method of treating seeds, a method of dipping seeds in a diluted or undiluted liquid preparation of the liquid or solid composition and thereby making the agent permeate into the seeds; a method of mixing a solid or liquid preparation with seeds for the sake of powder coating and thereby making the agent adhere to the seed surface; a method of mixing the preparation with an adhesive carrier such as resin, polymer or the like and coating seeds with such an adhesive mixture; a method of spraying the preparation to the neighborhood of seeds simultaneously with planting or the like can be referred to.

"Seed" to be treated with the seed treatment means a plant body of the initial stage of cultivation used for reproduction of plants, encompassing not only the seeds but also plant bodies for nutrient reproduction such as bulb, tuber, seed tuber, stock bud, aerial tuber, scaly bulb or stalks for cuttage or the like.

"Soil" or "cultivation carrier" for plants in carrying out the using method of the present invention means a support for the cultivation of a plant, in particular, a support in which the roots grow; their material quality is not limited, any material being acceptable as far as the plant can grow therein. For example, so-called soils, nursery mat, water or the like can be used, specific examples for the material being sand, pumice, vermiculite, diatomaceous earth, agar, gelatinous materials, polymeric materials, rock wool, glass wool, wood chips, bark or the like.

As the method for spraying onto foliage parts of crops or the like, spraying a liquid formulation such as an emulsifiable concentrate, flowable agent or the like or a solid formulation such as a wettable powder or wettable granule or the like having properly been diluted with water, spraying a dust, or fumigation or the like can be referred to.

As the method of soil application, applying a liquid preparation either diluted with water or undiluted onto the plant foot, nursery bed for raising seedlings or the like, spraying granules onto the plant foot or nursery bed, spraying a dust, a wettable powder, a wettable granule or granules onto the soil and mixing with the whole soil either before seeding or before transplantation, spraying a dust, wettable powder, wettable granule, granules or the like onto planting holes, planting rows or the like can be recited.

As the method for applying to a nursery box of paddy field rice, even though the preparation form may be varied depending on the time of application such as application at the sowing period, greening period or transplanting period, applying in the form of a dust, wettable granule, granules or the like can be recited. Application by mixing with the soil is also possible, which application is mixing with soil and a dust, wettable granule or granules, examples thereof being mixing into the bed soil, covering soil or whole soil. Further possible method is application by merely making the soil and various formulations into layers.

For applying to a paddy field, usually to a paddy field in a submerged state, a solid preparation such as a jumbo-pack, granules, wettable granules or the like or a liquid formulation such as a flowable, emulsifiable concentrate or the like are sprinkled. Otherwise, it is also possible to sprinkle or inject an appropriate agent as it is or in the form of a mixture with fertilizers into the soil at the time of transplantation.

Further possible is applying chemical solution of an emulsifiable concentrate to the water inlet or water flow source of the irrigating system, whereby a labor-saving application is achieved with water supplied.

In case of upland field crops, application to the cultivation carrier surrounding the seeds or plant bodies in the period from the seeding to the seedling raising is available. For plants where seeds are directly sown to the field, in addition to direct application to seeds, application onto the base of hills during the cultivation period is preferable. Sprinkling granules or irrigating with a liquid formulation after dilution with water or without dilution or the like is possible. Another preferable treatment is to mix granules with cultivation carriers before seeding and to sow seeds thereafter.

In cases where cultured plants to be transplanted are treated at the seeding time or in the seedling raising period, in addition to direct treatment onto seeds, irrigating treatment onto a seedling raising bed with a liquefied form or to sprinkling granules are preferable. Further, applying granules to the planting holes at the time of set-planting or mixing into the cultivation carrier in the neighborhood of the sites of transplantation are also preferable treatment.

The present inventive compound represented by the general formula (I) or salts thereof is in general used after having been formulated into a form which is convenient in use by the standard method for formulating agrochemicals.

Namely, the present inventive compound represented by the general formula (I) or salts thereof may be used after having been blended optionally together with an adjuvant in a proper proportion and prepared into a suitable preparation form such as suspension (flowable), emulsifiable concentrate, oil dispersions, soluble concentrate, wettable powder, wettable granules, granules, dust tablets, packs, jumbos, suspoemulsion or the like through dissolution, separation, suspension, mixing, impregnation, adsorption or sticking.

The present inventive agrohorticultural fungicides may contain in addition to the active ingredient, additive components which are commonly used for agricultural formulations if necessary. As such additive components, a carrier such as a solid carrier or a liquid carrier, a surfactant, a dispersant, a wetting agent, a binder, an adhesion-imparting agent, a thickener, a coloring agent, an extender, a spreader, an anti-freezing agent, an anti-caking agent, a disintegrating agent and a stabilizing agent or the like can be recited. Furthermore, an antiseptic agent, plant pieces may be used as additive components if necessary. These additive components may be used either alone or in combination of two or more.

As the solid carrier, for example, a natural mineral such as quartz, clay, kaolinite, pyrophillite, sericite, talc, bentonite, acid clay, attapulgite, zeolite or diatomaceous earth; an inorganic salt such as calcium carbonate, ammonium sulfate, sodium sulfate or potassium chloride, synthetic silicic acid or synthetic silicate; an organic solid carrier such as starch, cellulose or plant powder such as, for example, saw dust, coconut shellflower, corncob and tobacco stem; a plastic carrier such as polyethylene, polypropylene or polyvinylidene chloride; or urea, inorganic hollow materials, plastic hollow materials or fumed silica such as white carbon can be recited. These may be used either alone or in combination of two or more.

As the liquid carrier, for example, alcohols such as a monohydric alcohol such as methanol, ethanol, propanol, isopropanol or butanol or a polyhydric alcohol such as ethylene glycol, diethylene glycol, propylene glycol, hexylene glycol, polyethylene glycol, polypropylene glycol or glycerol; a polyhydric alcohol derivative such as propylene type glycol ether; a ketone such as acetone, methyl ethyl ketone, methyl isobutyl ketone, diisobutyl ketone or cyclohexanone; an ether such as ethyl ether, dioxane, ethylene glycol monoethyl ether, dipropyl ether or THF; an aliphatic hydrocarbon such as normal paraffin, naphthene, isoparaffin, kerosine or mineral oil; an aromatic hydrocarbon such as benzene, toluene, xylene, solvent naphtha or alkyl naphthalene; a halogenated hydrocarbon such as dichloroethane, chloroform or carbon tetrachloride; an ester such as ethyl acetate, diisopropyl phthalate, dibutyl phthalate, dioctyl phthalate or dimethyl adipate; a lactone such as [gamma]-butyrolactone; an amide such as dimethylformamide, diethylformamide, dimethylacetamide or N-alkylpyrrolidinone; a nitrile such as acetonitrile; a sulfur compound such as dimethylsulfoxide; a vegetable oil such as soybean oil, rapeseed oil, cotton oil or castor oil; or water can be recited. These may be used either alone or in combination of two or more.

As surfactants used as a dispersant or wetting agent, the following can be recited: a non-ionic surfactant such as a sorbitan fatty acid ester, a polyoxyethylene sorbitan fatty acid eater, a sucrose fatty acid ester, a polyoxyethylene fatty acid ester, a polyoxyethylene resin acid ester, a polyoxyethylene fatty acid diester, a polyoxyethylene alkyl ether, a polyoxyethylene alkyl phenyl ether, a polyoxyethylene dialkyl phenyl ether, a polyoxyethylene alkyl phenyl ether formalin condensate, a polyoxyethylene polyoxypropylene block copolymer, an alkyl polyoxyethylene polypropylene block polymer ether, a polyoxyethylene alkylamine, a polyoxyethylene fatty acid amide, a polyoxyethylene fatty acid bisphenyl ether, a polyalkylene benzyl phenyl ether, a polyoxyalkylene styryl phenyl ether, an acetylenediol, a polyoxyalkylene-added acetylenediol, a polyoxyethylene ether type silicon, an ester type silicon, a fluorinated surfactant, a polyoxyethylene castor oil or a polyoxyethylene hardened castor oil;

an anionic surfactant such as an alkyl sulfate, a polyoxyethylene alkyl ether sulfate, a polyoxyethylene alkyl phenyl ether sulfate, a polyoxyethylene styryl phenyl ether sulfate, an alkyl benzenesulfonate, a lignin sulfonate, an alkylsulfosuccinate, a naphthalenesulfonate, an alkylnaphthalenesulfonate, a salt of a formalin condensate of naphthalenesulfonate, a salt of a formalin condensate of an alkylnaphthalenesulfonate, a fatty acid salt, a polycarboxylic acid salt, an N-methyl-fatty acid sarcosinate, a resin acid salt, a polyoxyethylene alkyl ether phosphate or a polyoxyethylene alkyl phenyl ether phosphate;

a cationic surfactant such as a laurylamine hydrochloride, a stearylamine hydrochloride, an oleylamine hydrochloride, a stearylamine acetate, a stearylaminopropylamine acetate, an alkyltrimethylammonium chloride or an alkyldimethylbenzalkonium chloride; and an amphoteric surfactant such as an amino acid type or a betain type. These surfactants may be used either alone or in combination of two or more.

As the binder or adhesion-imparting agent, for example, carboxymethylcellulose or its salt, dextrin, water-soluble starch, xanthan gum, guar gum, sucrose, polyvinylpyrrolidone, gum arabic, polyvinyl alcohol, polyvinyl acetate, polysodium acrylate, a polyethylene glycol having an average molecular weight of 6,000 to 20,000, a polyethylene oxide having an average molecular weight of 100,000 to 5,000,000 or a natural phosphatide can be recited.

As the thickener, for example, a water-soluble polymer such as xanthan gum, guar gum, carboxylmethylcellulose, polyvinylpyrrolidone, carboxyvinyl polymer, an acrylic polymer, a starch compound or polysaccharide; or an inorganic fine powder such as high purity bentonite or white carbon can be recited.

As the coloring agent, for example, an inorganic pigment such as iron oxide, titanium oxide or Prussian blue; or an organic dye such as an arizarin dye, an azo dye or a metal phthalocyanine dye can be recited.

As the anti-freezing agent, for example, a polyhydric alcohol such as ethylene glycol, diethylene glycol, propylene glycol or glycerol can be recited.

As the additive component for an anti-caking agent or disintegrating agent, for example, starch, alginic acid, a polysaccharide such as mannose or galactose, polyvinylpyrrolidone, white carbon, ester gum or petroleum resin, sodium tripolyphosphate, sodium hexamethaphosphate, stearic acid metal salt, a cellulose powder, dextrin, a methacrylate copolymer, a polyvinylpyrrolidone, a polyaminocarboxylic acid chelate compound, a styrene sulfonate/isobutylene/maleic anhydride copolymer or a starch/polyacrylonitrile graft copolymer can be recited.

As the stabilizer, for example, a drying agent such as zeolite, quick lime or magnesium oxide; an anti-oxidation agent such as a phenol type, an amine type, a sulfur type or a phosphorus type; or an ultraviolet absorber such as a salicylic acid type or a benzophenone type can be recited.

As the antiseptic, for example, potassium sorbate or 1,2-benzthiazolin-3-one can be recited.

In addition, if necessary, a functional spreader, an activity enhancer such as piperonyl butoxide, an anti-freezing agent such as propylene glycol, an antioxidant such as BHT or other additive agents such as an UV absorber can be used.

The content of the active ingredient compound may be varied according to the need; the content can properly be selected from the range between 0.01 and 90 parts by weight in terms of 100 parts by weight of the present inventive agrohorticultural fungicide. For example, for dusts, granules, emulsifiable concentrates or wettable powders, the suitable content is from 0.01 to 50 parts by weight (0.01 to 50 weight % for the entire weight of the agrohorticultural fungicide).

The applying dosage of the harmful organism controlling agent of the present invention varies depending upon various factors such as, for example, a purpose, insect pests to be controlled, a growth state of a plant, tendency of insect pest emergence, weather, environmental conditions, a preparation form, an application method, an application site and an application time; the dosage of the active ingredient compound may be properly chosen in a range of 0.001 g to 10 kg, preferably 0.01 g to 1 kg per 10 ares depending upon the purpose.

In using the agrohorticultural fungicides comprising the present inventive compound of the general formula (I) or salts thereof, it is diluted to an appropriate concentration for spraying or treated as it is.

The present inventive agrohorticultural fungicides, in particular, the agrohorticultural insecticide can be used in admixture with other agrohorticultural insecticides, acaricides, nematocides, fungicides or biological pesticides, in order to expand both the spectrum of controllable diseases and pests, extend the controlling period or reduce the dosage; in addition, use in admixture with herbicides, plant growth regulators, fertilizer or the like depending on the use occasions. Representative compounds are recited below, which does not limit the scope.

As agrohorticultural fungicides to be used for such a purpose, the following agrohorticultural fungicides can be recited for example: aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isofetamid, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, enoxastrobin, epoxiconazole, oxadixyl, oxathiapiprolin, oxycarboxin, copper-8-quinolinolate, oxytetracycline, copper-oxinate, oxpoconazole, oxpoconazole-fumarate, oxolinic acid, octhilinone, ofurace, orysastrobin, soil fungicides such as carbam (metam-sodium); kasugamycin, carbamorph, carpropamid, carbendazim, carboxin, carvone, quinazamid, quinacetol, quinoxyfen, chinomethionat, quinomethionate, captafol, captan, kiralaxyl, quinconazole, quintozene, guazatine, cufraneb, cuprobam, coumoxystrobin, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, salicylanilide, zarilamid, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipymetitrone, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thifluzamide, thicyofen, thioquinox, thiram, decafentin, tecnazene, tecloftalam, tecoram, tetraconazole, debacarb, dehydroacetic acid, tebuconazole, tebufloquin, dodicin, dodine, DBEDC, dodemorph, drazoxolon, triadimenol, triadimefon, triazbutil, triazoxide, triamiphos, triarimol, trichlamide, triclopyricarb, tricyclazole, triticonazole, tridemorph, tributyltin oxide, triflumizole, trifloxystrobin, triforine, tolylfluanid, tolclofos-methyl, tolprocarb, natamycin, nabam, nitrostyrene, nitrothal-isopropyl, nuarimol, copper nonylphenol sulfonate, halacrinate, validamycin, valifenalate, harpin protein, picarbutrazox, bixafen, picoxystrobin, picobenzamide, bithionol, bitertanol, hydroxyisoxazole, hydroisoxazole-potassium, binapacryl, biphenyl, piperalin, hymexazol, pyraoxystrobin, pyracarbolid, pyraclostrobin, pyrazifluamid, pyrazophos, pyrametostrobin, pyriofenone, pyridinitril, pydiflumetofen, pydiflumetofen, pyrisoxazole, pyrifenox, pyribencarb, pyrimethanil, pyroxychlor, pyroxyfur, pyroquilon, vinclozolin, famoxadone, fenapanil, fenamidone, fenaminosulf, fenaminstrobin, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, benzovindiflupyr, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, mandestrobin, myclozolin, myclobutanil, mildiomycin, milneb, mecarbinzid, methasulfocarb, metazoxolon, metam, metam-sodium, metalaxyl, metalaxyl-M, metiram, methyl isothiocyanate, mepthyldinocap, metconazole, metsulfovax, methfuroxam, metominostrobin, metrafenone, mepanipyrim, mefenoxam, meptyldinocap, mepronil, mebenil, iodomethane, rabenzazole, methyl bromide, benzalkonium chloride, basic copper chloride, basic copper sulfate; inorganic fungicides such as silver or the like; sodium hypochlorote, cupric hydroxide, wettable sulfur, calcium polysulfide, potassium hydrogen carbonate, sodium hydrogen carbonate, sulfur, copper sulfate anhydride, nickel dimethyldithiocarbamate, oxine copper, zinc sulfate, copper sulfate pentahydrate or the like.

As agrohorticultural insecticides, acaricides, nematocides to be used for the same purpose, for example, the following are recited: 3,5-xylyl methylcarbamate (XMC), *Bacillus thuringiensis aizawai*, *Bacillus thuringiensis israelensis*, *Bacillus thuringiensis japonensis*, *Bacillus thuringiensis kurstaki*, *Bacillus thuringiensis tenebrionis*, crystal protein toxin produced by *Bacillus thuringiensis*, BPMC, Bt toxin insecticidal compound, CPCBS (chlorfenson), DCIP (dichlorodiisopropyl ether), D-D (1, 3-Dichloropropene), DDT, NAC., O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, afidopyropen, avermectin-B, amidoflumet, amitraz, alanycarb, aldicarb, aldoxycarb, aldrin, alpha-endosulfan, alpha-cypermethrin, albendazole, allethrin, isazofos, isamidofos, isoamidofos, isoxathion, isofenphos, isoprocarb: MIPC, epsilon-metofluthrin, epsilon-momfluorothrin, ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos: ESP, oxibendazole, oxfendazole, Potassium oleate, sodium oleate, cadusafos, kappa-bifenthrin, cartap, carbaryl, carbosulfan, carbofuryl, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorobenzilate, chlorobenzoate, chloroprallethrin, kelthane(dicofol, salithion, cyhalodiamide, cyanophos: CYAP, diafenthiuron, diamidafos, cyantraniliprole, theta-cypermethrin, dienochlor, cyenopyrafen, dioxabenzofos, diofenolan, sigma-cypermethrin, cyclaniliprole, dichlofenthion: ECP, cycloprothrin, dichlorvos: DDVP, disulfoton, dinotefuryl, cyhalothrin, cyphenothrin, cyfluthrin, diflubenzuron, cyflumetofen, diflovidazin, cyhexatin, cypermethrin, dimethylvinphos, dimethoate, dimefluthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, tioxazafen, thiodicarb, thiocyclam, thiosultap, thiosultap-sodium, thionazin, thiometon, deet, dieldrin, tetrachlorvinphos, tetradifon, tetraniliprole, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon: DEP, triflumezopyrim, triflumuron, tolfenpyrad, naled: BRP, nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, pyflubumide, bifenazate, bifenthrin, pymetrozine, pyraclorfos, pyrafluprole, pyridafenthion, pyridaben, pyridalyl, pyrifluquinazon, pyriprole, pyriproxyfen, pirimicarb, pyrimidifen, pyriminostrobin, pirimiphos-methyl, pyrethrins, fipronil, fenazaquin, fenamiphos, bromopropylate, fenitrothion: MEP, fenoxycarb, fenothiocarb, phenothrin, fenobucarb, fensulfothion, fenthion: MPP, phenthoate: PAP, fenvalerate, fenpyroximate, fenpropathrin, fenbendazole, fosthiazate, formetanate, butathiofos, buprofezin, furathiocarb, prallethrin, fluacrypyrim, fluazaindolizine, fluazinam, fluazuron, fluensulfone, fluxametamide, flucycloxuron, flucythrinate, fluvalinate, flufiprole, flupyradifurone, flupyrazofos, flufenerim, flufenoxystrobin, flufenoxuron, flufenzine, flufenoprox, fluproxyfen, flubrocythrinate, fluhexafon, flubendiamide, flumethrin, flurimfen, prothiofos, protrifenbute, flonicamid, propaphos, propargite: BPPS, profenofos, profluthrin, propoxur: PHC, flometoquin, bromopropylate, beta-cyfluthrin, hexaflumuron, hexythiazox, heptafluthrin, heptenophos, permethrin, benclothiaz, bendiocarb, bensultap, benzoximate, benfuracarb, phoxim, phosalone, fosthiazate, fosthietan, phosphamidon, phosphocarb, phosmet: PMP, polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion: DMTP, methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, momfluorothrin, lambda-cyhalothrin, ryanodine, lufenuron, rescalure, resmethrin, lepimectin, rotenone, levamisol hydrochloride, fenbutatin oxide, morantel tartarate, methyl bromide, cyhexatin, calcium cyanamide, calcium polysulfide, sulfur, nicotine-sulfate or the like.

As herbicides to be used for the same purpose, the following herbicides can be recited for example: 1-naphthylacetamide, 2, 4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPAthioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, iofensulfuron, isouron, isocarbamid, isoxachlortole, isoxapyrifop, isoflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalfluralin, ethiolate, ethychlozate ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlomitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, cyclopyrimorate, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, tiafenacil, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, triafamone, tri-allate, trietazine, tricamba, triclopyr, tridiphane, tritac, tritosulfuron, trifludimoxazin, triflusulfuron, triflusulfuron-methyl, trifluralin, trifloxysulfuron, tripropindan, tribenuron-methyl, tribenuron, trifop, trifopsime, trimeturon, tolpyralate, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, halauxifen, haloxyfop, haloxyfop-P, haloxyfop-methyl, halosafen, halosulfuron, halosulfuron-methyl, picloram, picolinafen, bicyclopyrone, ispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenquinotrione, fenthiaprop, fenteracol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, romacil, brompyrazon, prometryn, prometon, bromoxynil, bromofenoxim, bromobutide, bromobonil, florasulam, florpyrauxifen, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide, methyl bromide or the like.

Further, as biological agrochemicals, the same effect can be achieved by the use mixed with the following biological agrochemicals for example: virus formulations such as nuclear polyhedrosis virus (NPV), granulosis virus (GV), cytoplasmic polyhedrosis virus (CPV), Entomopox virus (EPV) or the like; microbial agrochemicals known as insecticidal or nematocidal agents such as *Monacrosporium phymatophagum, Steinernema carpocapsae, Steinernema kushidai, Pasteuria penetrans* or the like; microbial agrochemicals used as fungicidal agents such as *Trichoderma lignorum, Agrobacterium radiobactor*, nonpathogenic *Erwinia carotovora, Bacillus subtilis* or the like; and biological agrochemicals utilized as herbicides such as *Xanthomonas campestris* or the like.

Furthermore, co-use with biological agrochemicals such as, for example, natural enemies such as *Encarsia* wasp (*Encarsia formosa*), colemani wasp (*Aphidius colemani*), aphid midge (*Aphidoletes aphidimyza*), warm weather leafminer parasitoid (*Diglyphus isaea*), leafminer parasitoid (*Dacnusa sibirica*), Persimilis (*Phytoseiulus persimilis*), springtails (*Amblyseius cucumeris*), anthocorid predatory bug (*Orius sauteri*) or the like; microbial agrochemicals such as Beauveria brongniartii; and pheromone agents such as (Z)-10-tetradecenyl=acetate, (E,Z)-4,10-tetradecadienyl=acetate, (Z)-8-dodecenyl=acetate, (Z)-11-tetradecenyl=acetate, (Z)-13-icocene-10-one, 14-methyl-1-octadecene or the like is also possible.

Representative examples of the present invention are recited but the present invention is not limited thereto.

EXAMPLES

Production Example 1

Production of N-(methoxyl{5-[5-(trifluoromethyl)-1,2,4-oxadiazol-3-yl]thiophen-2-yl}methyl)butylamide (Compound 1-13)

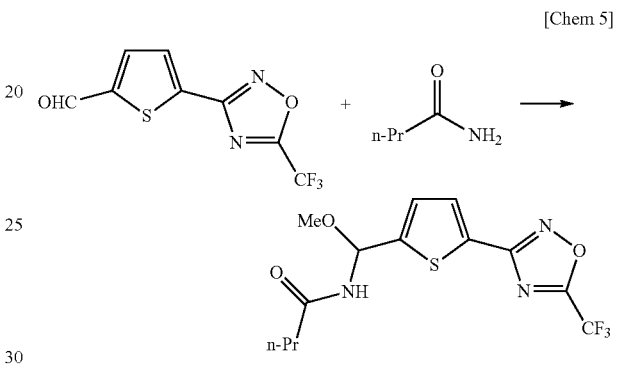

[Chem 5]

5-[5-(trifluoromethyl)-1,2,4-oxadiazol-3-yl]thiophene-2-carboaldehyde (0.27 g, 1.1 mmol) was dissolved in chloroform (12 mL) under the argon atmosphere, butylamide (0.11 g, 1.3 mmol) and titanium(IV) methoxide (0.33 g, 1.9 mmol) were added, stirred while heating at 45° C. for 7.2 hours, and thereafter allowed to stand for 16 hours at room temperature. Then the temperature was raised to 45° C., and the mixture was stirred for 8 hours and then allowed to stand at room temperature for 16 hours. After that, silica gel was added and the mixture was stirred for 15 min and then concentrated under reduced pressure. The residue obtained was purified by silica gel column chromatography to obtain the title compound (0.12 g, 0.34 mmol).

Yield: 32%

Physical property: Melting point 147-148° C.

Reference Example 1

Production of 2-(5-bromothiophen-2-yl)-1,3-dioxolane

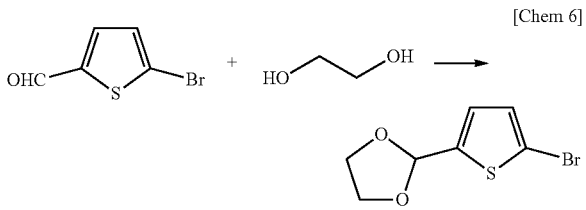

[Chem 6]

5-bromothiophene-2-carboaldehyde (13 g, 68 mmol) was dissolved in toluene (120 mL), and ethylene glycol (17 g, 272 mmol), p-toluenesulfonic acid (17 g, 272 mmol) and p-toluenesulfonic acid monohydrate (1.3 g, 6.8 mmol) were added, and, while removing water using a Dean-Stark apparatus, the mixture was refluxed while heating for 4 hours. After completion of the reaction, the mixture was returned to room temperature, and the reaction was stopped by adding saturated aqueous sodium bicarbonate solution and extracted with ethyl acetate. The organic layer was washed with saturated brine, dried over sodium sulfate, and concentrated under reduced pressure to obtain the title compound (17 g, 71 mmol).

Yield: 104%
Physical property:Refractive index 1.3432(24.6)

Reference Example 2

Production of
5-(1,3-dioxolan-2-yl)thiophene-2-carbonitrile

[Chem 7]

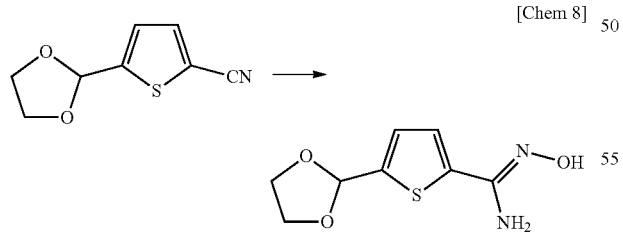

2-(5-bromothiophen-2-yl)-1,3-dioxolane (17 g, 71 mmol) was dissolved in DMA (35 mL) and copper cyanide (I) (7.0 g, 78 mmol) was added, and the mixture was stirred while at 150° C. for 5.5 hours. After completion of the reaction, the mixture was returned to room temperature and filtered through Celite. 4% aqueous ammonia solution was added to stop the reaction, and the mixture was extracted with ethyl acetate. The organic layer was washed with saturated brine, dried over sodium sulfate, and concentrated under reduced pressure. The residue obtained was purified by silica gel column chromatography to obtain the title compound (6.5 g, 36 mmol).

Yield: 50%
Physical property:Refractive index 1.3454 (23.0)

Reference Example 3

Production of (Z)-5-(1,3-dioxolan-2-yl)-N'-hydroxy-thiophene-2-carboximidamide

[Chem 8]

5-(1,3-dioxolan-2-yl)thiophene-2-carbonitrile (6.5 g, 36 mmol) was dissolved in ethanol (70 mL), and triethylamine (5.4 g, 54 mmol) was added. Triethylamine (5.4 g, 54 mmol) and hydroxylamine hydrochloride (3.7 g, 54 mmol) were added, and the mixture was stirred under heated reflux for 3 hours. Water was then added, ethanol was removed under reduced pressure, and the mixture was extracted with ethyl acetate. The organic layer was washed with saturated brine, dried over sodium sulfate, and concentrated under reduced pressure. The residue obtained was purified by silica gel column chromatography to obtain the title compound (5.1 g, 24 mmol).

Yield: 66%
Physical property: Melting point 131-133° C.

Reference Example 4

Production of 3-[5-(1,3-dioxolan-2-yl)thiophen-2-yl]5-(trifluoromethyl)-1,2,4-oxadiazole

[Chem 9]

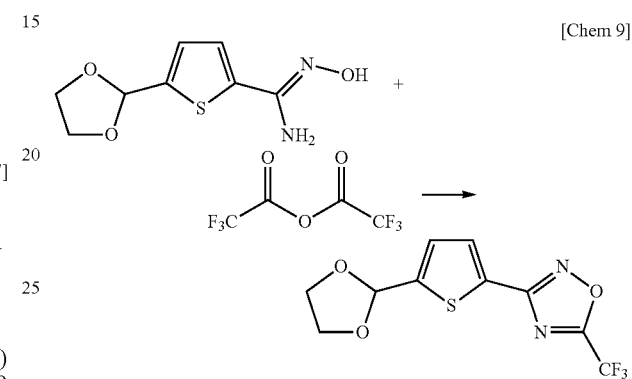

(Z)-5-(1,3-dioxolan-2-yl)-N'-hydroxythiophene-2-carboxyimidamide (4.4 g, 21 mmol) was dissolved in chloroform (50 mL), pyridine (9.7 g, 124 mmol) and trifluoroacetic anhydride (8.7 g, 41 mmol) were added, and the mixture was stirred at room temperature for 4.5 hours. Water was then added and the mixture was extracted with chloroform. The organic layer was washed with saturated brine, dried over sodium sulfate, and concentrated under reduced pressure. The residue was purified by silica gel column chromatography to obtain the title compound (4.5 g, 15 mmol).

Yield: 74%
Physical property: Melting point 44-45° C.

Reference Example 5

Production of 5-[5-(trifluoromethyl)-1,2,4-oxadiazol-3-yl]thiophene-2-carboaldehyde

[Chem 10]

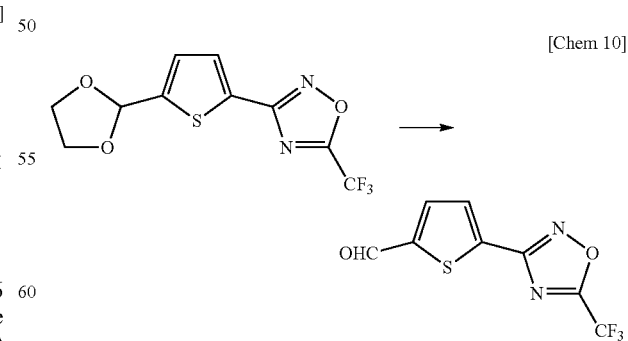

3-[5-(1,3-dioxolan-2-yl)thiophen-2-yl]5-(trifluoromethyl)-1,2,4-oxadiazole (4.4 g, 15 mmol) was dissolved in 1,4-dioxane 45 (ml) and 2M hydrochloric acid solution (45 ml, 90 mmol) was added, and the mixture was stirred for 4 hours at room temperature. Saturated aqueous sodium bicarbonate solution was then added and extracted with ethyl acetate. The organic layer was washed with saturated brine, dried over sodium sulfate, and concentrated under reduced pressure to obtain the title compound (3.7 g, 15 mmol).

Yield: 99%

Physical property: Melting point 56-57° C.

Formulation examples are recited but the present invention is not limited thereto. In the formulation examples, the term "parts" denotes "parts by weight".

Formulation Example 1

| Present inventive compound represented by the general formula (I) | 10 parts |
|---|---|
| Xylene | 70 parts |
| N-methylpyrrolidone | 10 parts |
| Mixture of polyoxyethylene nonylphenyl ether and calcium alkylbenzenesulfonate | 10 parts |

An emulsifiable concentrate was prepared by uniformly mixing and dissolving the above ingredients.

Formulation Example 2

| Present inventive compound represented by the general formula (I) | 3 parts |
|---|---|
| Clay powder | 82 parts |
| Diatomaceous earth powder | 15 parts |

A dust was prepared by mixing uniformly and grinding the above ingredients.

Formulation Example 3

| Present inventive compound represented by the general formula (I) | 5 parts |
|---|---|
| Mixed powder of bentonite and clay | 90 parts |
| Calcium lignin sulfonate | 5 parts |

Granules were prepared by mixing the above ingredients uniformly together with a suitable amount of water, and kneading the resulting mixture, followed by granulation and drying.

Formulation Example 4

| Present inventive compound represented by the general formula (I) | 20 parts |
|---|---|
| Kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

Test Example 1. Fungicidal Efficacy Test for Soybean Rust

A chemical agent prepared according to Formulation Examples 1 to 4 containing the present inventive compound represented by the general formula (I) as an active ingredient was diluted with water to a predetermined concentration. Soybeans (cultivar: Enrei, 2-leaf stage) grown in pots of 6 cm in diameter were foliage sprayed at a rate of 10 ml per pot. After air-drying the solution, the spore suspension prepared from spores obtained from soybean leaves infected with soybean rust (Phakopsora pachyrhizi) was spray-inoculated, kept at 20° C. humidified conditions for 24 hours, and then transferred to a greenhouse to be left about 10 days.

For evaluation, various diseased area ratios were assessed to calculate the control value from the following formula 1.

$$\text{Control value (\%)} = \frac{\text{Average lesion area ratio in untreated plot} - \text{Average lesion area ratio in treated plot}}{\text{Average lesion area ratio in untreated plot}} \times 100 \quad \text{[Formula 1]}$$

Assessment Criteria

0: Control value 9% or lower
1: Control value 10-19%
2: Control value 20-29%
3: Control value 30-39%
4: Control value 40-49%
5: Control value 50-59%
6: Control value 60-69%
7: Control value 70-79%
8: Control value 80-89%
9: Control value 90-99%
10: Control value 100%

As the result of the above mentioned test, of the present inventive compounds represented by the general formula (I), 1-13, 1-22, 1-25, 1-43, 1-47, 1-91, 1-101, 1-107 and 1-109 showed an effect with a control value of 8 or higher at the treatment concentration of 50 ppm.

INDUSTRIAL APPLICABILITY

The present inventive compound represented by the general formula (I) or salts thereof has a remarkable effect as an agrohorticultural fungicide.

The invention claimed is:

1. A compound of formula (I) or a salt thereof:

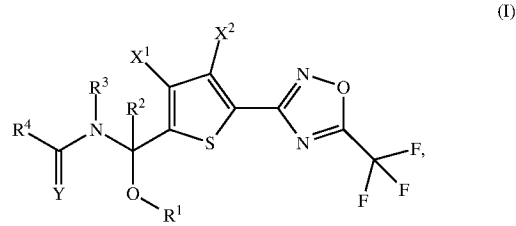

wherein
$R^1$ is
(a1) a hydrogen atom;
(a2) a ($C_1$-$C_6$)alkyl group;
(a3) a ($C_2$-$C_6$)alkenyl group;
(a4) a ($C_2$-$C_6$)alkynyl group;
(a5) a ($C_3$-$C_6$)cycloalkyl group;
(a6) a halo ($C_1$-$C_6$)alkyl group;
(a7) a halo ($C_2$-$C_6$)alkenyl group;
(a8) a halo ($C_2$-$C_6$)alkynyl group; or
(a9) a halo ($C_3$-$C_8$)cycloalkyl group,
$R^2$ is (b1) a hydrogen atom;
(b2) a $(C_1\text{-}C_6)$alkyl group;
(b3) a $(C_2\text{-}C_6)$alkenyl group;
(b4) a $(C_2\text{-}C_6)$alkynyl group;
(b5) a $(C_3\text{-}C_6)$cycloalkyl group;
(b6) a halo $(C_1\text{-}C_6)$alkyl group;
(b7) a halo $(C_2\text{-}C_6)$alkenyl group;
(b8) a halo $(C_2\text{-}C_6)$alkynyl group; or
(b9) a halo $(C_3\text{-}C_8)$cycloalkyl group,
$R^3$ is
(c1) a hydrogen atom;
(c2) a $(C_1\text{-}C_6)$alkyl group;
(c3) a $(C_2\text{-}C_6)$alkenyl group;
(c4) a $(C_2\text{-}C_6)$alkynyl group;
(c5) a $(C_3\text{-}C_6)$cycloalkyl group;
(c6) a $(C_1\text{-}C_6)$alkylcarbonyl group; or
(c7) a $(C_1\text{-}C_6)$alkoxycarbonyl group,
$R^4$ is
(d1) a hydrogen atom;
(d2) a $(C_1\text{-}C_6)$alkyl group;
(d3) a $(C_2\text{-}C_6)$alkenyl group;
(d4) a $(C_2\text{-}C_6)$alkynyl group;
(d5) a $(C_3\text{-}C_6)$cycloalkyl group;
(d6) a $(C_1\text{-}C_6)$alkoxyl group;
(d7) a halo $(C_1\text{-}C_6)$alkyl group;
(d8) a halo $(C_2\text{-}C_6)$alkenyl group;
(d9) a halo $(C_2\text{-}C_6)$alkynyl group;
(d10) a halo $(C_3\text{-}C_8)$cycloalkyl group;
(d11) a halo $(C_1\text{-}C_6)$alkoxyl group;
(d12) a $R^a(R^b)N$ group wherein $R^a$ and $R^b$ are each independently a hydrogen atom, $(C_1\text{-}C_6)$alkyl group, $(C_3\text{-}C_6)$cycloalkyl group, $(C_3\text{-}C_6)$cycloalkyl $(C_1\text{-}C_6)$alkyl group, phenyl group, $(C_1\text{-}C_6)$alkylcarbonyl group or phenylcarbonyl group;
(d13) an aryl group;
(d14) an aryl group each independently having on the ring 1 to 8 substituents selected from the group consisting of a halogen atom, cyano group, nitro group, $(C_1\text{-}C_6)$alkyl group, $(C_1\text{-}C_6)$alkoxy group, $(C_3\text{-}C_6)$cycloalkyl group, halo $(C_1\text{-}C_6)$alkyl group, halo $(C_1\text{-}C_6)$alkoxy group, halo $(C_3\text{-}C_6)$cycloalkyl group, $(C_1\text{-}C_6)$alkylthio group, $(C_1\text{-}C_6)$alkylsulfinyl group, $(C_1\text{-}C_6)$alkylsulfonyl group, halo $(C_1\text{-}C_6)$alkylthio group, halo $(C_1\text{-}C_6)$alkylsulfinyl group and halo $(C_1\text{-}C_6)$alkylsulfonyl group;
(d15) a heteroaryl group;
(d16) a heteroaryl group each independently having on the ring 1 to 3 substituents selected from the group consisting of a halogen atom, cyano group, nitro group, $(C_1\text{-}C_6)$alkyl group, $(C_1\text{-}C_6)$alkoxy group, $(C_3\text{-}C_6)$cycloalkyl group, halo $(C_1\text{-}C_6)$alkyl group, halo $(C_1\text{-}C_6)$alkoxy group, halo $(C_3\text{-}C_6)$cycloalkyl group, $(C_1\text{-}C_6)$alkylthio group, $(C_1\text{-}C_6)$alkylsulfinyl group, $(C_1\text{-}C_6)$alkylsulfonyl group, halo $(C_1\text{-}C_6)$alkylthio group, halo $(C_1\text{-}C_6)$alkylsulfinyl group and halo $(C_1\text{-}C_6)$alkylsulfonyl group;
(d17) an aryl $(C_1\text{-}C_6)$alkyl group;
(d18) an aryl $(C_1\text{-}C_6)$alkyl group each independently having on the ring 1 to 8 substituents selected from the group consisting of a halogen atom, cyano group, nitro group, $(C_1\text{-}C_6)$alkyl group, $(C_1\text{-}C_6)$alkoxy group, $(C_3\text{-}C_6)$cycloalkyl group, halo $(C_1\text{-}C_6)$alkyl group, halo $(C_1\text{-}C_6)$alkoxy group, halo $(C_3\text{-}C_6)$cycloalkyl group, $(C_1\text{-}C_6)$alkylthio group, $(C_1\text{-}C_6)$alkylsulfinyl group, $(C_1\text{-}C_6)$alkylsulfonyl group, halo $(C_1\text{-}C_6)$alkylthio group, halo $(C_1\text{-}C_6)$alkylsulfinyl group and halo $(C_1\text{-}C_6)$alkylsulfonyl group;
(d19) a heteroaryl $(C_1\text{-}C_6)$alkyl group;
(d20) a heteroaryl $(C_1\text{-}C_6)$alkyl group each independently having on the ring 1 to 3 substituents selected from the group consisting of a halogen atom, cyano group, nitro group, $(C_1\text{-}C_6)$alkyl group, $(C_1\text{-}C_6)$alkoxy group, $(C_3\text{-}C_6)$cycloalkyl group, halo $(C_1\text{-}C_6)$alkyl group, halo $(C_1\text{-}C_6)$alkoxy group, halo $(C_3\text{-}C_6)$cycloalkyl group, $(C_1\text{-}C_6)$alkylthio group, $(C_1\text{-}C_6)$alkylsulfinyl group, $(C_1\text{-}C_6)$alkylsulfonyl group, halo $(C_1\text{-}C_6)$alkylthio group, halo $(C_1\text{-}C_6)$alkylsulfinyl group and halo $(C_1\text{-}C_6)$alkylsulfonyl group;
(d21) a $(C_1\text{-}C_6)$alkyl group each independently having on the chain 1 to 3 substituents selected from the group consisting of a cyano group, $(C_1\text{-}C_6)$alkoxyl group, $R^a(R^b)N$ group wherein $R^a$ and $R^b$ have the same meaning as mentioned above, $(C_1\text{-}C_6)$alkylthio group, $(C_1\text{-}C_6)$alkylsulfinyl group and $(C_1\text{-}C_6)$alkylsulfonyl group; or
(d22) a tetrahydropyranyl group,
$X^1$ and $X^2$ are each independently
(e1) a hydrogen atom;
(e2) a halogen atom;
(e3) a cyano group;
(e4) a nitro group;
(e5) a $(C_1\text{-}C_6)$alkyl group;
(e6) a $(C_3\text{-}C_6)$cycloalkyl group;
(e7) a $(C_1\text{-}C_6)$alkoxyl group;
(e8) a halo $(C_1\text{-}C_6)$alkyl group;
(e9) a halo $(C_1\text{-}C_6)$alkoxyl group;
(e10) a halo $(C_3\text{-}C_6)$cycloalkyl group;
(e11) a $(C_1\text{-}C_6)$alkylthio group;
(e12) a $(C_1\text{-}C_6)$alkylsulfinyl group;
(e13) a $(C_1\text{-}C_6)$alkylsulfonyl group;
(e14) a halo $(C_1\text{-}C_6)$alkylthio group;
(e15) a halo $(C_1\text{-}C_6)$alkylsulfinyl group; or
(e16) a halo $(C_1\text{-}C_6)$alkylsulfonyl group, and
Y is an oxygen atom or a sulfur atom.

2. The compound according to claim 1 or a salt thereof, wherein
$R^1$ is (a2) a $(C_1\text{-}C_6)$alkyl group,
$R^2$ is (b1) a hydrogen atom,
$R^3$ is
(c1) a hydrogen atom;
(c2) a $(C_1\text{-}C_6)$alkyl group; or
(c5) a $(C_3\text{-}C_6)$cycloalkyl group,
$R^4$ is
(d2) a $(C_1\text{-}C_6)$alkyl group;
(d3) a $(C_2\text{-}C_6)$alkenyl group;
(d4) a $(C_2\text{-}C_6)$alkynyl group;
(d5) a $(C_3\text{-}C_6)$cycloalkyl group;
(d6) a $(C_1\text{-}C_6)$alkoxyl group;
(d7) a halo $(C_1\text{-}C_6)$alkyl group;
(d12) a $R^a(R^b)N$ group wherein $R^a$ and $R^b$ are each independently a hydrogen atom, $(C_1\text{-}C_6)$alkyl group, $(C_3\text{-}C_6)$cycloalkyl group, $(C_3\text{-}C_6)$cycloalkyl $(C_1\text{-}C_6)$alkyl group, phenyl group, $(C_1\text{-}C_6)$alkylcarbonyl group or phenylcarbonyl group;
(d13) an aryl group;
(d14) an aryl group each independently having on the ring 1 to 8 substituents selected from the group consisting of a halogen atom, cyano group, nitro group, $(C_1\text{-}C_6)$alkyl group, $(C_1\text{-}C_6)$alkoxy group, $(C_3\text{-}C_6)$cycloalkyl group, halo $(C_1\text{-}C_6)$alkyl group, halo $(C_1\text{-}C_6)$alkoxy group, halo $(C_3\text{-}C_6)$cycloalkyl group, $(C_1\text{-}C_6)$alkylthio group, $(C_1\text{-}C_6)$alkylsulfinyl group, $(C_1\text{-}C_6)$alkylsulfonyl group, halo $(C_1\text{-}C_6)$alkylthio group, halo $(C_1\text{-}C_6)$alkylsulfinyl group and halo $(C_1\text{-}C_6)$alkylsulfonyl group;
(d15) a heteroaryl group;
(d17) an aryl $(C_1\text{-}C_6)$alkyl group;

(d21) a $(C_1-C_6)$alkyl group each independently having on the chain 1 to 3 substituents selected from the group consisting of a cyano group, $(C_1-C_6)$alkoxyl group, $R^a(R^b)N$ group wherein $R^a$ and $R^b$ have the same meaning as mentioned above, $(C_1-C_6)$alkylthio group, $(C_1-C_6)$alkylsulfinyl group and $(C_1-C_6)$alkylsulfonyl group; or
(d22) a tetrahydropyranyl group,
$X^1$ and $X^2$ are each independently
(e1) a hydrogen atom;
(e2) a halogen atom;
(e5) a $(C_1-C_6)$alkyl group;
(e7) a $(C_1-C_6)$alkoxyl group;
(e11) a $(C_1-C_6)$alkylthio group;
(e12) a $(C_1-C_6)$alkylsulfinyl group; or
(e13) a $(C_1-C_6)$alkylsulfonyl group, and
Y is an oxygen atom or a sulfur atom.

3. The compound according to claim 1 or a salt thereof, wherein
$R^3$ is (c1) a hydrogen atom,
$R^4$ is
(d2) a $(C_1-C_6)$alkyl group;
(d4) a $(C_2-C_6)$alkynyl group;
(d5) a $(C_3-C_6)$cycloalkyl group;
(d7) a halo $(C_1-C_6)$alkyl group;
(d13) an aryl group; or
(d21) a $(C_1-C_6)$alkyl group each independently having on the chain 1 to 3 substituents selected from the group consisting of a cyano group, $(C_1-C_6)$alkoxyl group, $R^a(R^b)N$ group wherein $R^a$ and $R^b$ have the same meaning as mentioned above, $(C_1-C_6)$alkylthio group, $(C_1-C_6)$alkylsulfinyl group and $(C_1-C_6)$alkylsulfonyl group,
$X^1$ and $X^2$ are each independently
(e1) a hydrogen atom, and
Y is an oxygen atom.

4. A fungicide characterized by having as an active ingredient a compound according to claim 1 or a salt thereof.

5. A method of controlling plant disease comprising the step of treating a plant or soil with an effective amount of the fungicide according to claim 4.

6. A method of controlling plant disease comprising the step of treating a plant or soil with an effective amount of a compound according to claim 1 or a salt thereof.

* * * * *